United States Patent
Itoi

(10) Patent No.: US 10,844,059 B2
(45) Date of Patent: Nov. 24, 2020

(54) HETEROCYCLIC COMPOUND AND ORGANIC ELECTROLUMINESCENCE DEVICE INCLUDING THE SAME

(71) Applicant: Samsung Display Co., Ltd., Yongin-si (KR)

(72) Inventor: Hiroaki Itoi, Yokohama (KR)

(73) Assignee: Samsung Display Co., Ltd., Yongin-si (KR)

( * ) Notice: Subject to any disclaimer, the term of this patent is extended or adjusted under 35 U.S.C. 154(b) by 351 days.

(21) Appl. No.: 15/805,012

(22) Filed: Nov. 6, 2017

(65) Prior Publication Data

US 2018/0134706 A1   May 17, 2018

(30) Foreign Application Priority Data

Nov. 17, 2016   (KR) .................... 10-2016-0153490

(51) Int. Cl.
*C07D 471/06* (2006.01)
*H01L 51/00* (2006.01)
(Continued)

(52) U.S. Cl.
CPC .......... *C07D 471/06* (2013.01); *C07D 498/06* (2013.01); *C07F 7/0816* (2013.01);
(Continued)

(58) Field of Classification Search
CPC .. C07B 59/001; C07D 471/06; C07D 498/06; C07F 7/0816; H01L 51/0052;
(Continued)

(56) References Cited

U.S. PATENT DOCUMENTS 9,502,667 B2   11/2016   Saito et al.
2018/0331301 A1*  11/2018  Parham ............... H01L 51/0072

FOREIGN PATENT DOCUMENTS

JP   2009-29726 A    2/2009
JP   2009-267255 A   11/2009
(Continued)

OTHER PUBLICATIONS

Machine translation for WO 2016/105165 (publication date Jun. 2016). (Year: 2016).*
(Continued)

*Primary Examiner* — Dawn L Garrett
(74) *Attorney, Agent, or Firm* — Lewis Roca Rothgerber Christie LLP

(57) ABSTRACT

A heterocyclic compound may be represented by Formula 1. The heterocyclic compound may be included in an organic electroluminescence device. The organic electroluminescence device including the heterocyclic compound according to an embodiment of the present disclosure may attain high emission efficiency and a low driving voltage effect.

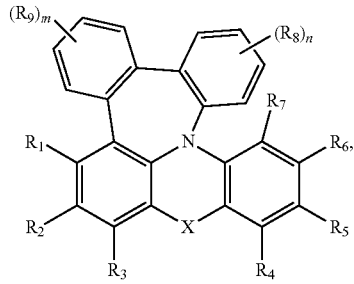

Formula 1 where X is O, S, $NR_{10}$, $CR_{11}R_{12}$ or $SiR_{13}R_{14}$.

20 Claims, 1 Drawing Sheet

(51) Int. Cl.
*C07D 498/06* (2006.01)
*C07F 7/08* (2006.01)
*H01L 51/50* (2006.01)

(52) U.S. Cl.
CPC ...... *H01L 51/0052* (2013.01); *H01L 51/0071* (2013.01); *H01L 51/0072* (2013.01); *H01L 51/0073* (2013.01); *H01L 51/0094* (2013.01); *H01L 51/0058* (2013.01); *H01L 51/5056* (2013.01)

(58) Field of Classification Search
CPC ............. H01L 51/0058; H01L 51/0071; H01L 51/0072; H01L 51/0073; H01L 51/0094; H01L 51/5056; C09K 11/06
See application file for complete search history.

(56) References Cited

FOREIGN PATENT DOCUMENTS

| | | | |
|---|---|---|---|
| JP | 2014-160813 A | | 9/2014 |
| KR | 10-2015-0077220 | * | 7/2015 |
| KR | 10-2016-0079715 A | | 7/2016 |
| WO | WO 2016/080791 A1 | | 5/2016 |
| WO | WO 2016/102039 A1 | * | 6/2016 |
| WO | WO 2016/105165 A2 | * | 6/2016 |

OTHER PUBLICATIONS

Machine translation for KR 10-2015-0077220 (publication date Jul. 2015) (Year: 2015).*

* cited by examiner

HETEROCYCLIC COMPOUND AND ORGANIC ELECTROLUMINESCENCE DEVICE INCLUDING THE SAME

CROSS-REFERENCE TO RELATED APPLICATION

This application claims priority to and the benefit of Korean Patent Application No. 10-2016-0153490, filed on Nov. 17, 2016, the entire content of which is hereby incorporated by reference.

BACKGROUND

One or more aspects of embodiments of the present disclosure are directed toward a heterocyclic compound and an organic electroluminescence device including the same.

Recently, development of an organic electroluminescence display as an image display is being actively conducted. An organic electroluminescence display is a self-luminescent display and is different from a liquid crystal display, for example, in that it accomplishes the display of images by recombining holes and electrons respectively injected from a first electrode and a second electrode in an emission layer and emitting light via an organic luminescent material included in the emission layer.

An example organic electroluminescence device may be composed of a first electrode, a hole transport layer disposed (e.g., positioned) on the first electrode, an emission layer disposed on the hole transport layer, an electron transport layer disposed on the emission layer, and a second electrode disposed on the electron transport layer. Holes are injected from the first electrode, for example, and the injected holes may move via the hole transport layer to be injected into the emission layer. Meanwhile, electrons are injected from the second electrode, for example, and the injected electrons may move via the electron transport layer to be injected into the emission layer. By recombining the holes and electrons injected into the emission layer, excitons are generated in the emission layer. The organic electroluminescence device emits light using during the transition of the excitons back to a ground state. However, the configuration of an organic electroluminescence device is not limited to those described above, and various modifications may be possible.

SUMMARY

One or more aspects of embodiments of the present disclosure are directed toward a heterocyclic compound and an organic electroluminescence device including the same. More particularly, embodiments of the present disclosure provide a heterocyclic compound which may be used as a hole transport material and an organic electroluminescence device including the heterocyclic compound in a hole transport region.

An embodiment of the present disclosure provides a heterocyclic compound represented by the following Formula 1:

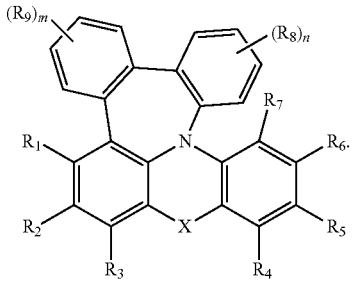

Formula 1

In Formula 1, X may be O, S, $NR_{10}$, $CR_{11}R_{12}$ or $SiR_{13}R_{14}$; $R_1$ to $R_{14}$ may each independently be selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring; $R_{11}$ and $R_{13}$ may each independently form a ring by combining with $R_{12}$ and $R_{14}$, respectively; and m and n may each independently be an integer of 0 to 4.

In an embodiment, in Formula 1, $R_1$ to $R_9$ may not form a ring by combining with an adjacent group selected from $R_1$ to $R_9$.

In an embodiment, Formula 1 may be represented by the following Formula 2:

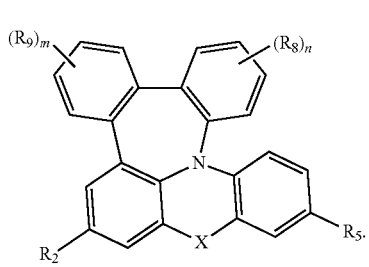

Formula 2

In Formula 2, definitions for X, $R_2$, $R_5$, $R_8$, $R_9$, n and m may each independently be the same as those provided above, and at least one of $R_2$ or $R_5$ may be a substituted or unsubstituted aryl group having 6 to 30 carbon atoms for forming a ring, or a substituted or unsubstituted heterocyclic group having 2 to 30 carbon atoms for forming a ring.

In an embodiment, at least one of $R_2$ or $R_5$ in Formula 2 may be a substituted or unsubstituted phenyl group, a substituted or unsubstituted naphthyl group, a substituted or unsubstituted carbazole group, or a substituted or unsubstituted dibenzofuranyl group.

In an embodiment, in Formula 1, $R_5$ may be represented by the following Formula 3:

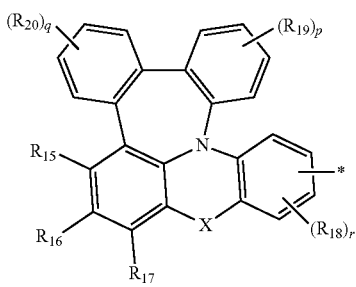

Formula 3

In Formula 3, Y may be O, S, $NR_{21}$, $CR_{22}R_{23}$ or $SiR_{24}R_{25}$; $R_{15}$ to $R_{25}$ may each independently be selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring; $R_{22}$ and $R_{24}$ may each independently form a ring by combining with $R_{23}$ and $R_{25}$, respectively; r may be an integer of 0 to 3; and p and q may each independently be an integer of 0 to 4.

In an embodiment, X in Formula 1 and Y in Formula 3 may be the same.

In an embodiment, X may be $CR_{11}R_{12}$, and $R_{11}$ and $R_{12}$ may each independently be a substituted or unsubstituted alkyl group having 1 to 20 carbon atoms, or a substituted or unsubstituted aryl group having 6 to 30 carbon atoms for forming a ring, and $R_{11}$ and $R_{12}$ may optionally form a ring by combining with each other in Formula 1.

In an embodiment, in Formula 1, X may be O, and at least one of $R_1$ to $R_7$ may be a substituted or unsubstituted aryl group having 6 to 30 carbon atoms for forming a ring, or a substituted or unsubstituted heterocyclic group having 2 to 30 carbon atoms for forming a ring.

In an embodiment, in Formula 1, X may be S, and at least one of $R_1$ to $R_7$ may be a substituted or unsubstituted aryl group having 6 to 30 carbon atoms for forming a ring, or a substituted or unsubstituted heterocyclic group having 2 to 30 carbon atoms for forming a ring.

In an embodiment, in Formula 1, X may be $SiR_{13}R_{14}$, and $R_{13}$ and $R_{14}$ may each independently be a substituted or unsubstituted alkyl group having 1 to 20 carbon atoms, or a substituted or unsubstituted aryl group having 6 to 30 carbon atoms for forming a ring, and $R_{13}$ and $R_{14}$ may optionally form a ring by combining with each other.

An embodiment of the present disclosure provides an organic electroluminescence device including a first electrode, a hole transport region disposed on the first electrode, an emission layer disposed on the hole transport region, an electron transport region disposed on the emission layer, and a second electrode disposed on the electron transport region, in which the hole transport region includes a heterocyclic compound according to an embodiment of the present disclosure.

In an embodiment, the hole transport region may include a hole injection layer disposed on the first electrode and a hole transport layer disposed on the hole injection layer, and the hole transport layer may include the heterocyclic compound according to an embodiment of the present disclosure.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
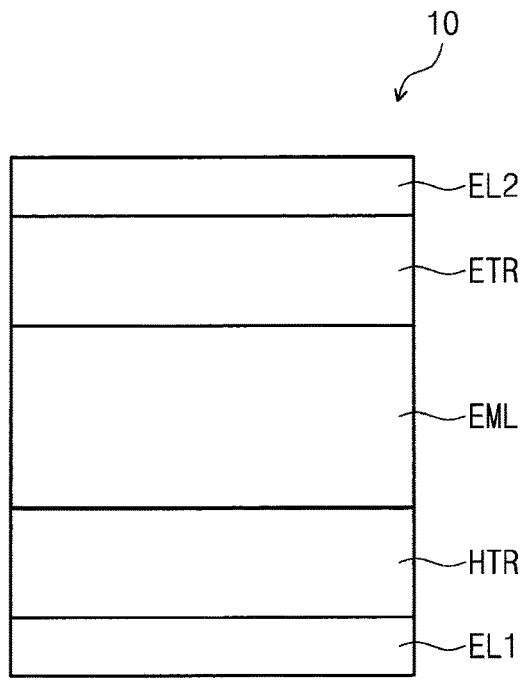
FIG. 1 is a schematic cross-sectional view of an organic electroluminescence device according to an embodiment of the present disclosure.

The above objects, other objects, features and advantages of the present disclosure will be easily understood from the description of the example embodiments with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

Like reference numerals refer to like elements throughout the specification and drawings. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" or "under" another element, it can be directly on or under the other element, or intervening elements may also be present. Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

In the present disclosure, ——* may refer to a binding site (e.g., to a neighboring atom).

In the present disclosure, "substituted or unsubstituted" may refer to a functional group being either unsubstituted or substituted with at least one substituent selected from deuterium, halogen, cyano group, nitro group, amino group, silyl group, boron, phosphine oxide, aryl phosphine, phosphine sulfide, alkyl, alkenyl, aryl and heterocyclic group. In addition, each of the substituent above may be itself be substituted or unsubstituted. For example, biphenyl group may be referred to as an aryl group, or a phenyl group substituted with a phenyl group.

In the present disclosure, "forming a ring by combining adjacent groups with each other" may refer to forming a substituted or unsubstituted hydrocarbon ring (cyclic group) or a substituted or unsubstituted heterocyclic group by combining adjacent groups with each other. In addition, a ring formed by combining adjacent groups with each other may be further connected (or coupled) with another ring to form a spiro structure. The term "hydrocarbon ring" may include an aliphatic hydrocarbon ring and an aromatic hydrocarbon ring. The hydrocarbon ring may be a monocycle or a polycycle.

In the present disclosure, examples of a halogen atom include a fluorine atom, a chlorine atom, a bromine atom, and an iodine atom, but are not limited thereto.

In the present disclosure, the alkyl group may have a linear, branched or cyclic form. The carbon number of the alkyl group may be 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group may refer to a functional group or a substituent derived from an aromatic hydrocarbon ring. The aryl group may be a monocyclic aryl or a polycyclic aryl group. The carbon number of the aryl group for forming a ring may be 6 to 30, 6 to 20, or 6 to 15. Herein, "atoms for forming a ring" may refer to ring-forming atoms of a given moiety. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the present disclosure, the fluorenyl group may be substituted, and two adjacent substituents of the fluorenyl group may be combined with each other to form a spiro structure.

In the present disclosure, the heterocyclic group may include an aliphatic heterocyclic group and an aromatic heterocyclic group, and the aromatic heterocyclic group may be a heteroaryl group. The heterocyclic group may be a monocycle or a polycycle.

In the present disclosure, the heteroaryl group may include at least one of O, N, P, Si, or S as a ring-forming heteroatom. The carbon number of the heteroaryl group for forming a ring may be 2 to 30, 2 to 20, or 2 to 15. The heteroaryl group may be monocyclic heteroaryl or polycyclic heteroaryl. Polycyclic heteroaryl may have bicyclic or tricyclic structure, for example. Examples of the heteroaryl may include thienyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazinyl, phthalazinyl, pyrido pyrimidinyl, pyrido pyrazinyl, pyrazino pyrazinyl, isoquinolinyl, indolyl, carbazolyl, N-arylcarbazolyl, N-heteroaryl carbazolyl, N-alkyl carbazolyl, benzoxazolyl, benzoimidazolyl, benzothiazolyl, benzocarbazolyl, benzothienyl, dibenzothiophenyl, thienothienyl, benzofuranyl, phenanthrolinyl, thiazolyl, isoxazolyl, oxadiazolyl, thiadiazolyl, benzothiazolyl, phenothiazinyl, dibenzosilolyl, dibenzofuranyl, etc., without limitation.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boron and aryl boron. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the carbon number of the amino group is not specifically limited, and may be 1 to 30. The amino group may include alkyl amino and aryl amino. Examples of the amino group may include methylamino, dimethylamino, phenylamino, diphenylamino, naphthylamino, 9-methyl-anthracenylamino, triphenylamino, etc., without limitation.

Hereinafter, the heterocyclic compound according to an embodiment of the present disclosure will be explained.

The heterocyclic compound according to an embodiment of the present disclosure is represented by the following Formula 1:

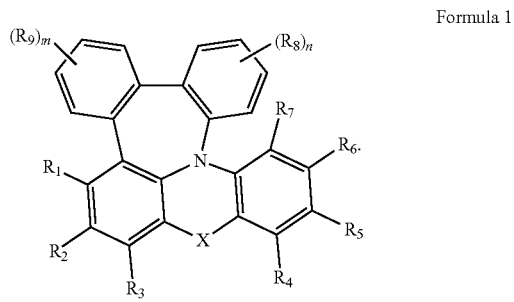

Formula 1

In Formula 1, X may be O, S, $NR_{10}$, $CR_{11}R_{12}$ or $SiR_{13}R_{14}$; $R_1$ to $R_{14}$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heterocyclic group having 2 to 30 carbon atoms for forming a ring; $R_{11}$ and $R_{13}$ may each independently form a ring by combining with $R_{12}$ and $R_{14}$, respectively; and m and n may each independently be an integer of 0 to 4.

When n is an integer of 2 or more, a plurality of $R_9$ may be the same or different from each other. When m is an integer of 2 or more, a plurality of $R_9$ may be the same or different from each other.

At least one of $R_1$ to $R_7$ may be substituted with a substituent other than hydrogen. However, embodiments of the present disclosure are not limited thereto, and each of $R_1$ to $R_7$ may be hydrogen.

For example, compound of Formula 1 may be represented by the following Formula 2:

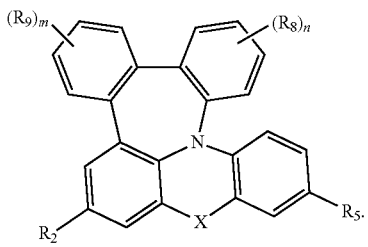

Formula 2

In Formula 2, definitions of X, $R_2$, $R_5$, $R_8$, $R_9$, n and m are the same as those provided above, and at least one of $R_2$ or $R_5$ is a substituted or unsubstituted aryl group having 6 to 30 carbon atoms for forming a ring, or a substituted or unsubstituted heterocyclic group having 2 to 30 carbon atoms for forming a ring.

In Formula 2, $R_2$ and $R_5$ may each independently be a substituted or unsubstituted aryl group having 6 to 30 carbon atoms for forming a ring, or a substituted or unsubstituted heteroaryl group having 2 to 30 carbon atoms for forming a ring. $R_2$ and $R_5$ may be the same.

In Formula 2, at least one of $R_2$ or $R_5$ may be a substituted or unsubstituted phenyl group, a substituted or unsubstituted naphthyl group, a substituted or unsubstituted carbazolyl group, or a substituted or unsubstituted dibenzofuranyl group. For example, $R_5$ may be a carbazolyl group substituted with carbazole. However, an embodiment of the present disclosure is not limited thereto.

In Formula 2, n and m may each independently be 0. However, an embodiment of the present disclosure is not limited thereto.

In Formula 1, $R_5$ may be represented by the following Formula 3:

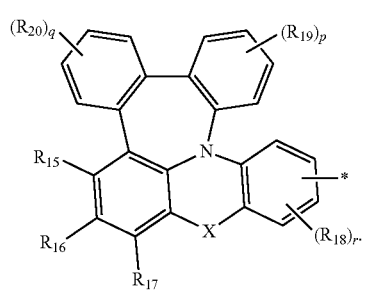

Formula 3

In Formula 3, Y may be O, S, $NR_{21}$, $CR_{22}R_{23}$ or $SiR_{24}R_{25}$; $R_{15}$ to $R_{25}$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heterocyclic group having 2 to 30 carbon atoms for forming a ring; $R_{22}$ and $R_{24}$ may each independently form a ring by combining with $R_{23}$ and $R_{25}$, respectively; r may be an integer of 0 to 3; and p and q may each independently be an integer of 0 to 4.

In Formula 3, when r is an integer of 2 or more, a plurality of $R_{18}$ may be the same or different from each other. When p is an integer of 2 or more, a plurality of $R_{19}$ may be the same or different from each other. When q is an integer of 2 or more, a plurality of $R_{20}$ may be the same or different from each other.

In embodiments where $R_5$ is represented by Formula 3, the heterocyclic compound according to an embodiment of the present disclosure may include two same heterocycles. For example, X in Formula 1 and Y in Formula 3 may be the same as each other. In addition, all of $R_1$ to $R_4$ and $R_6$ to $R_9$ in Formula 1 may be hydrogen, and all of $R_{15}$ to $R_{20}$ in Formula 3 may be hydrogen.

X may be $CR_{11}R_{12}$, and $R_{11}$ and $R_{12}$ may each independently be a substituted or unsubstituted alkyl group having 1 to 20 carbon atoms, or a substituted or unsubstituted aryl group having 6 to 30 carbon atoms for forming a ring, and $R_{11}$ and $R_{12}$ may optionally form a ring by combining with each other. Although an embodiment of the present disclosure is not limited thereto, $R_{11}$ and $R_{12}$ may be the same as each other. For example, each of $R_{11}$ and $R_{12}$ may be a substituted or unsubstituted methyl. As another example, each of $R_{11}$ and $R_{12}$ may be a substituted or unsubstituted phenyl. Furthermore, $R_{11}$ and $R_{12}$ may combine with each other to form a fluorene ring.

X may be O, and at least one of $R_1$ to $R_7$ may be a substituted or unsubstituted aryl group having 6 to 30 carbon atoms for forming a ring, or a substituted or unsubstituted heterocyclic group having 2 to 30 carbon atoms for forming a ring. For example, $R_5$ may be a substituted or unsubstituted aryl group having 6 to 30 carbon atoms for forming a ring, or a substituted or unsubstituted heterocyclic group having 2 to 30 carbon atoms for forming a ring. As another example, $R_2$ and $R_5$ may each independently be a substituted or unsubstituted aryl group having 6 to 30 carbon atoms for forming a ring, or a substituted or unsubstituted heteroaryl group having 2 to 30 carbon atoms for forming a ring.

In an embodiment, X may be S, and at least one of $R_1$ to $R_7$ may be a substituted or unsubstituted aryl group having 6 to 30 carbon atoms for forming a ring, or a substituted or unsubstituted heterocyclic group having 2 to 30 carbon atoms for forming a ring. For example, $R_5$ may be a substituted or unsubstituted aryl group having 6 to 30 carbon atoms for forming a ring, or a substituted or unsubstituted heterocyclic group having 2 to 30 carbon atoms for forming a ring. As another example, $R_2$ and $R_5$ may each independently be a substituted or unsubstituted aryl group having 6 to 30 carbon atoms for forming a ring, or a substituted or unsubstituted heteroaryl group having 2 to 30 carbon atoms for forming a ring.

In an embodiment, X may be $SiR_{13}R_{14}$, and $R_{13}$ and $R_{14}$ may each independently be a substituted or unsubstituted alkyl group having 1 to 20 carbon atoms, or a substituted or unsubstituted aryl group having 6 to 30 carbon atoms for forming a ring, and $R_{13}$ and $R_{14}$ may optionally form a ring by combining with each other. Although an embodiment of the present disclosure is not limited thereto, $R_{13}$ and $R_{14}$ may be the same as each other. For example, each of $R_{13}$ and $R_{14}$ may be a substituted or unsubstituted methyl. As another example, each of $R_{13}$ and $R_{14}$ may be a substituted or unsubstituted phenyl. Furthermore, $R_{13}$ and $R_{14}$ may combine with each other to form a fluorene ring.

In an embodiment, X may be $NR_{10}$, and $R_{10}$ may be a substituted or unsubstituted alkyl group having 1 to 10 carbon atoms, or a substituted or unsubstituted aryl group having 6 to 15 carbon atoms for forming a ring.

n and m may each independently be 0. However, an embodiment of the present disclosure is not limited thereto. In an embodiment, at least one of n or m may be 1 or more, and at least one of $R_8$ or $R_9$ may be substituted with a substituent other than hydrogen.

The heterocyclic compound represented by Formula 1 may be any one selected from the following Compounds 1-32 (collectively denoted as Compound Group 1).
Compound Group1
1
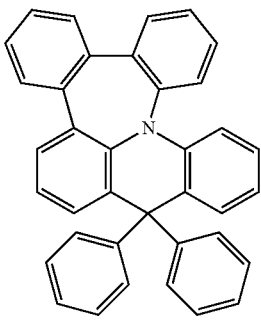
2
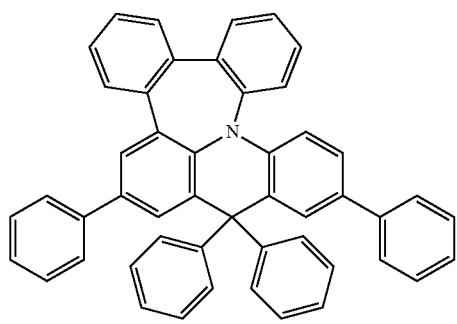
3
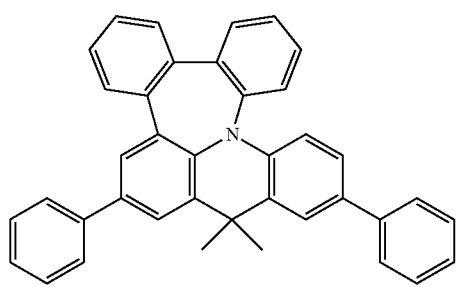
4
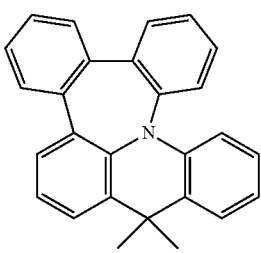
-continued
5
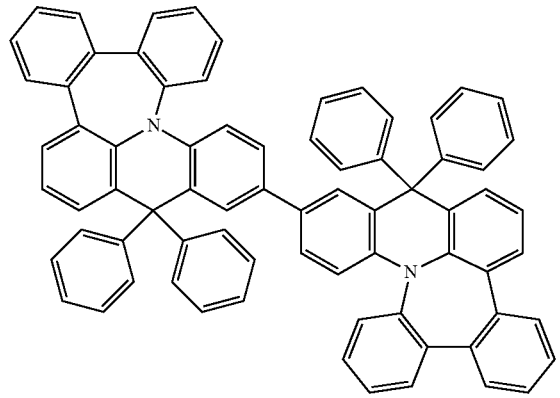
6
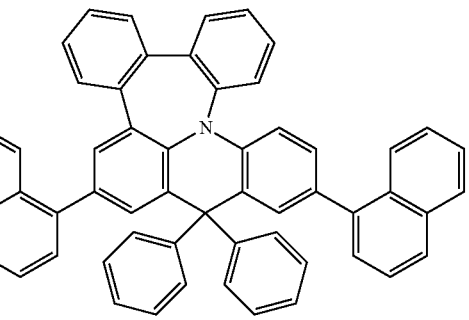
7
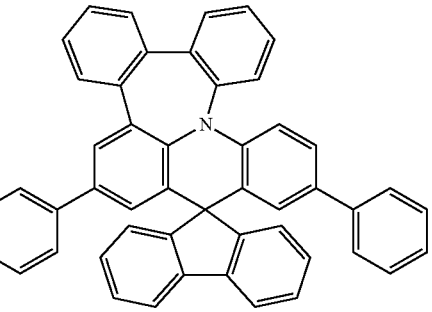
8
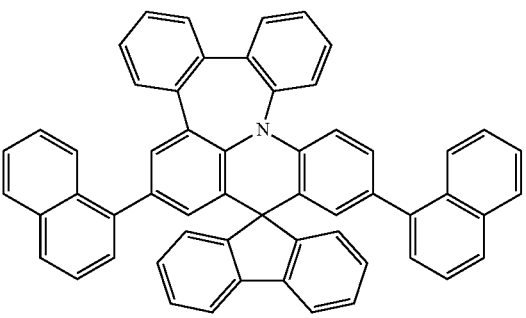

9
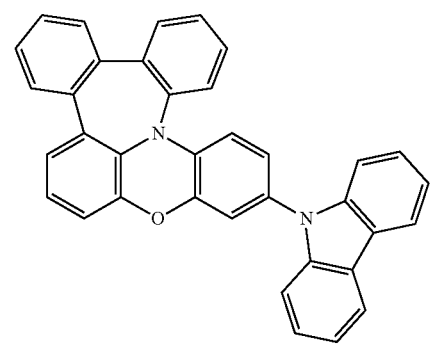
10
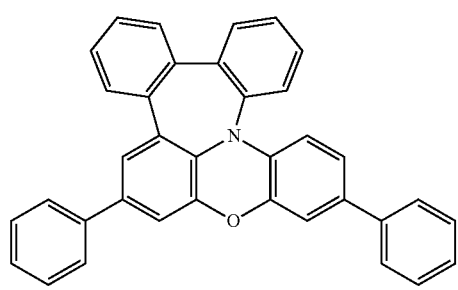
11
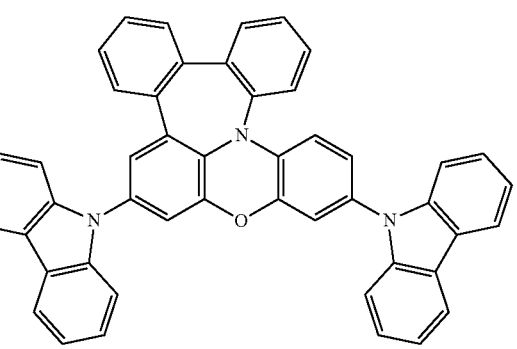
12
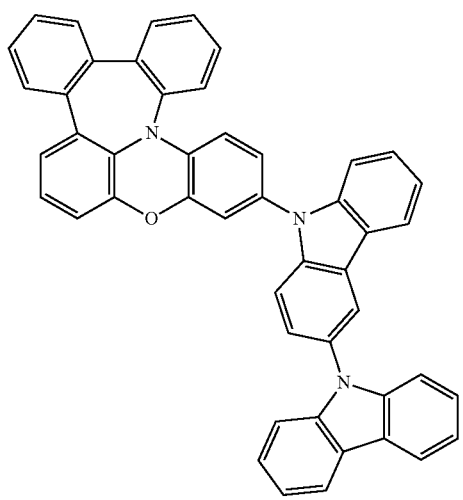
13
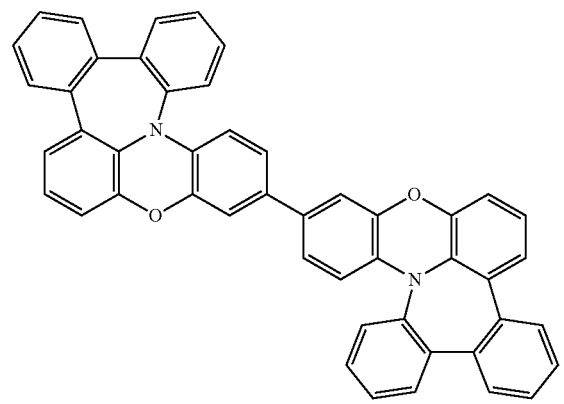
14
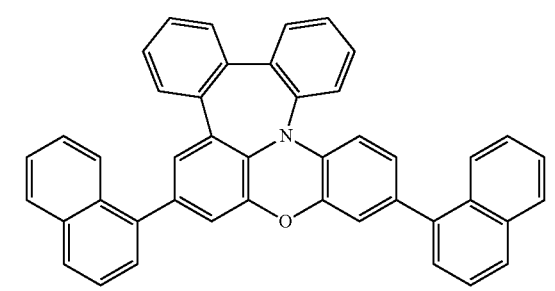
15
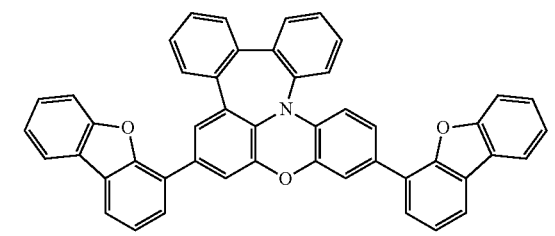
16
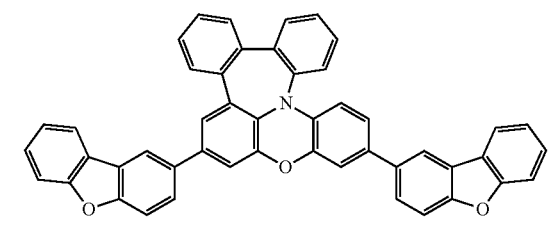
17
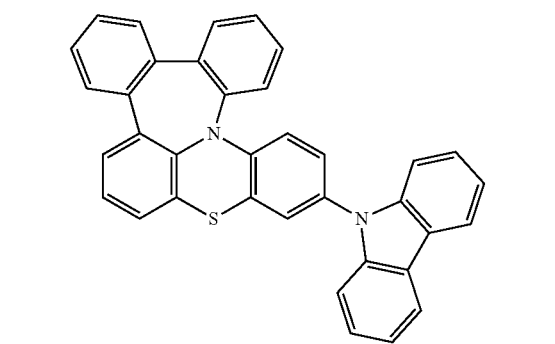

18
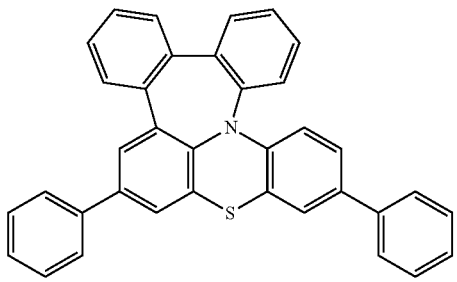
19
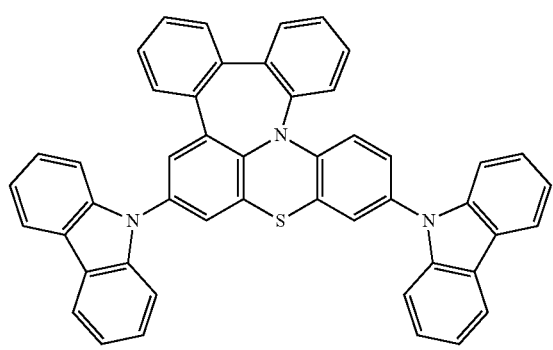
20
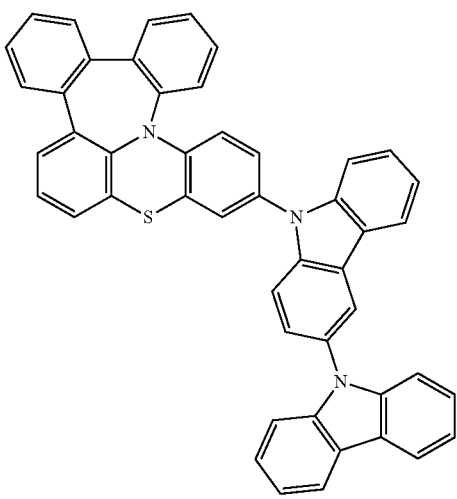
21
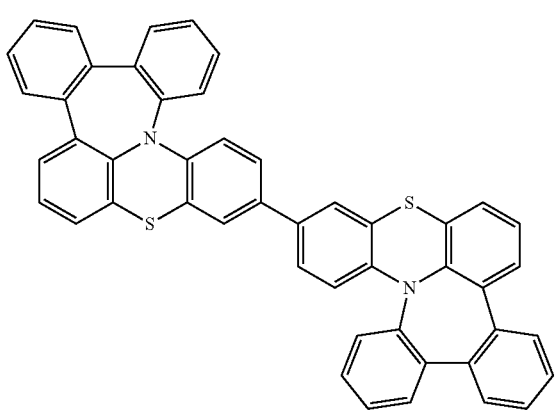
22
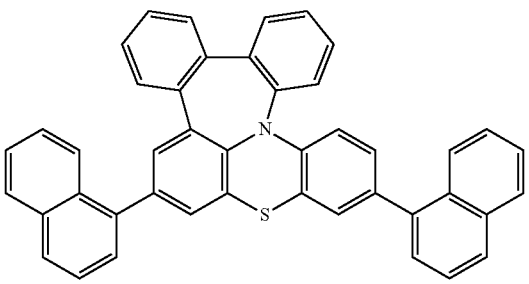
23
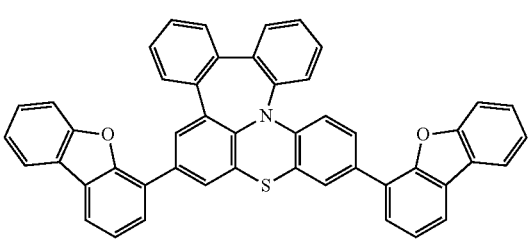
24
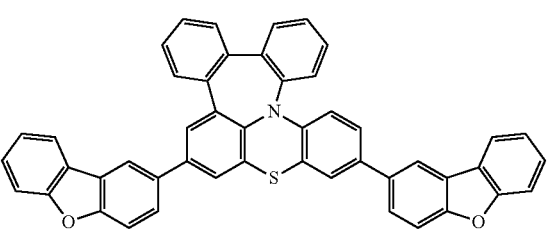
25
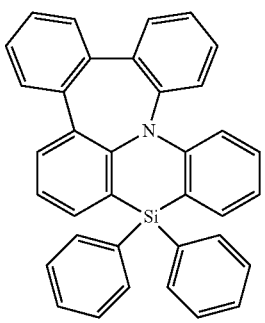
26
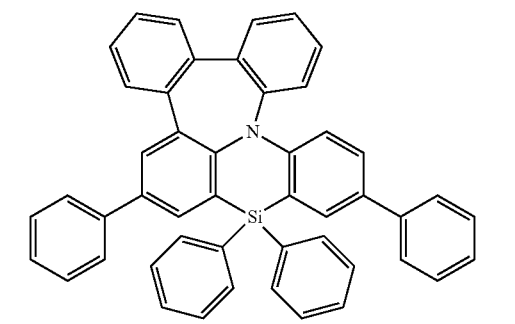

27

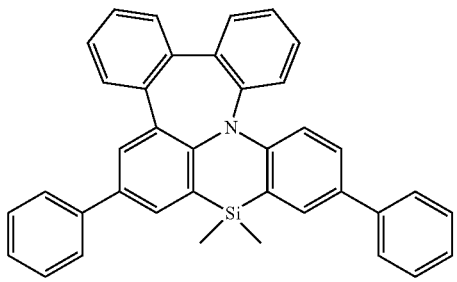

28

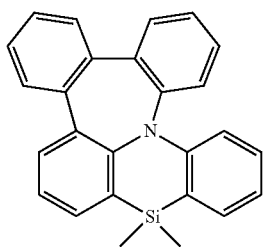

29

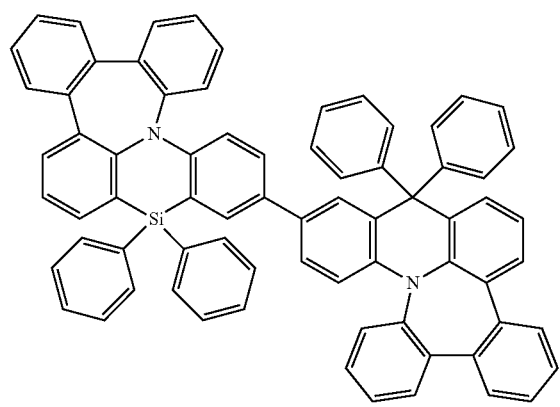

30

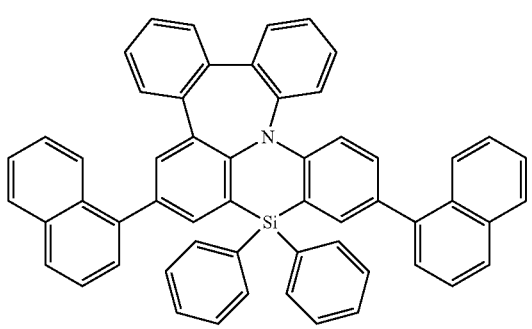

31

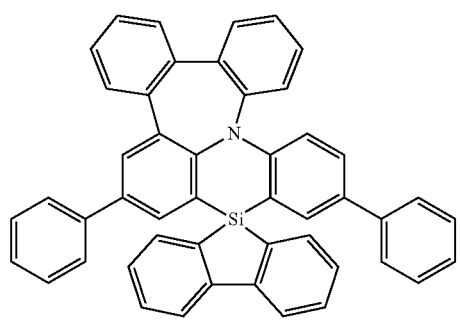

32

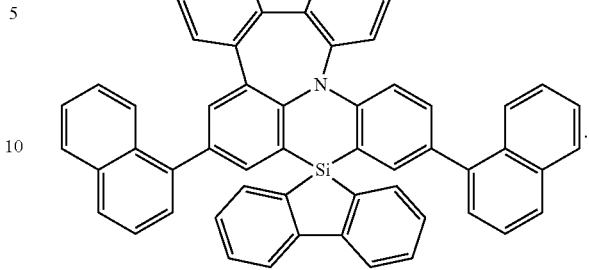

The heterocyclic compound represented by Formula 1 may be used as a material for an organic electroluminescence device. For example, the heterocyclic compound represented by Formula 1 may be used as a hole transport material.

When the heterocyclic compound according to an embodiment of the present disclosure is applied to an organic electroluminescence device, the device may attain a high efficiency and/or low driving voltage effect.

Hereinafter, an organic electroluminescence device according to an embodiment of the present disclosure will be explained in more detail. The following description will primarily focus on the features other than the above-described heterocyclic compound according to an embodiment of the present disclosure, and aspects that are not described below should be apparent from the above-provided description on the heterocyclic compound according to an embodiment of the present disclosure.

An organic electroluminescence device according to an embodiment of the present disclosure includes the heterocyclic compound according to an embodiment of the present disclosure.

Figure 2:
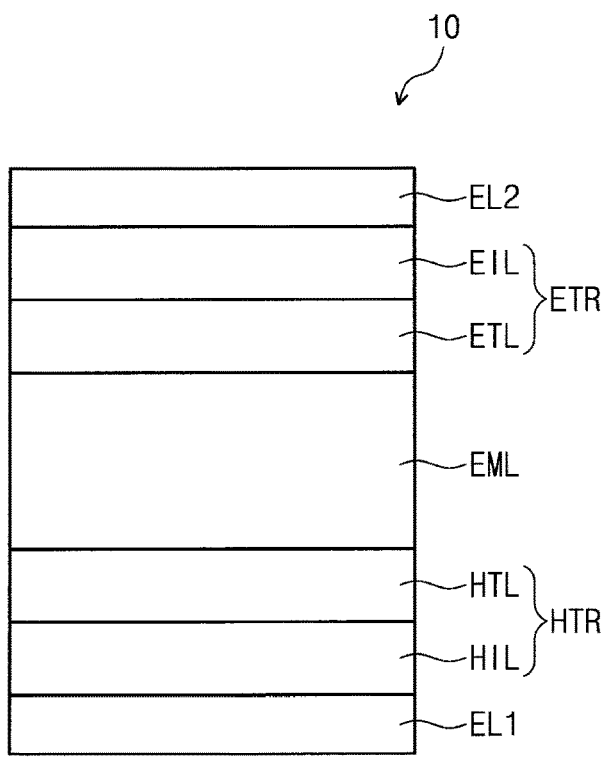
FIG. 2 is a schematic cross-sectional view of an organic electroluminescence device according to an embodiment of the present disclosure.

FIG. 1 is a schematic cross-sectional view illustrating an organic electroluminescence device according to an embodiment of the present disclosure. FIG. 2 is a schematic cross-sectional view illustrating an organic electroluminescence device according to an embodiment of the present disclosure.

Referring to FIGS. 1 and 2, an organic electroluminescence device 10 according to an embodiment of the present disclosure includes a first electrode EL1, a hole transport region HTR, an emission layer EML, an electron transport region ETR, and a second electrode EL2.

The first electrode EL1 has conductivity (e.g., the first electrode EL1 may be a conductor). The first electrode EL1 may be a pixel electrode or an anode. The first electrode EL1 may be a transmissive electrode, a transflective electrode, or a reflective electrode. In embodiments where the first electrode EL1 is a transmissive electrode, the first electrode EL1 may include a transparent metal oxide such as indium tin oxide (ITO), indium zinc oxide (IZO), zinc oxide (ZnO), and/or indium tin zinc oxide (ITZO). In embodiments where the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, and/or a mixture thereof (e.g., a mixture of Ag and Mg). The first electrode EL1 may have a structure including a plurality of layers including a reflective layer and/or transflective layer formed using any of the above-described materials, and a transparent conductive layer formed using ITO, IZO, ZnO, and/or ITZO.

The thickness of the first electrode EL1 may be from about 1,000 Å to about 10,000 Å, for example, from about 1,000 Å to about 3,000 Å.

The hole transport region HTR my be disposed (e.g., positioned) on the first electrode EL1. The hole transport region HTR may include at least one of a hole injection layer HIL, a hole transport layer HTL, a hole buffer layer, and an electron blocking layer.

Hereinafter, a case where the heterocyclic compound according to an embodiment of the present disclosure is included in a hole transport region HTR, will be explained. However, embodiments of the present disclosure are not limited thereto. For example, the heterocyclic compound according to an embodiment of the present disclosure may be included in at least one organic layer provided between the first electrode EL1 and the second electrode EL2. For example, the heterocyclic compound according to an embodiment of the present disclosure may be included in the emission layer EML.

The hole transport region HTR may include the heterocyclic compound according to an embodiment of the present disclosure. For example, the hole transport region HTR may include the heterocyclic compound represented by the following Formula 1:

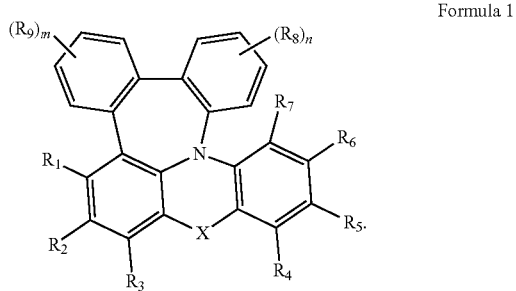

Formula 1

In Formula 1, definitions of $R_1$ to $R_9$, X, n and m are respectively the same as those provided above, and thus will not be provided again. The compound represented by Formula 1 included in the hole transport region HTR may be a monoamine compound.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, laminated (stacked) in this order from the first electrode EL1, without limitation.

In case where the hole transport region HTR has a structure of hole injection layer HIL/hole transport layer HTL, the heterocyclic compound according to an embodiment of the present disclosure may be included in the hole transport layer HTL, and in this case, the hole transport layer HTL may be contact the emission layer EML. However, embodiments of the present disclosure are not limited thereto. For example, when the hole transport region HTR has a multilayer structure, the heterocyclic compound according to an embodiment of the present disclosure may be included in a layer contacting the emission layer EML, and may be included in the layer contacting the emission layer EML and in the hole transport layer HTL. When the hole transport layer HTL is said to include the heterocyclic compound according to an embodiment of the present disclosure, the hole transport layer HTL may include one or more identical or different heterocyclic compounds according to an embodiment of the present disclosure.

The hole transport region HTR may be formed using various methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f:2',3'-h] quinoxaline-2,3,6,7,10,11-hexacarbonitrile (HAT-CN), etc.

When the hole transport layer HTL includes the heterocyclic compound according to an embodiment of the present disclosure, it may include only the heterocyclic compound according to an embodiment of the present disclosure. Alternatively, the hole transport layer HTL may further include any suitable material, in addition to the heterocyclic compound according to an embodiment of the present disclosure. For example, the hole transport layer HTL may further include carbazole derivatives (such as N-phenyl carbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, for example, from about 100 Å to about 1,000 Å. In case when the hole transport region HTR includes both of the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. When the thicknesses of the hole transport region HTR, the hole injection layer HIL and the hole transport layer HTL satisfy any of the above-described ranges, satisfactory (or suitable)

hole transport properties may be obtained without the substantial increase of a driving voltage.

The hole transport region HTR may further include a charge generating material, in addition to the above-described materials, to improve conductivity. The charge generating material may be dispersed in the hole transport region HTR uniformly or non-uniformly. The charge generating material may be, for example, a p-dopant. The p-dopant may be one of quinone derivatives, metal oxides, and cyano group-containing compounds, without limitation. Non-limiting examples of the p-dopant may include quinone derivatives (such as tetracyanoquinodimethane (TCNQ) and/or 2,3,5,6-tetrafluoro-tetracyanoquinodimethane (F4-TCNQ)), metal oxides (such as tungsten oxide and/or molybdenum oxide), and the like, without limitation.

As described above, the hole transport region HTR may further include at least one of a hole buffer layer and an electron blocking layer, in addition to the hole injection layer HIL and the hole transport layer HTL. The hole buffer layer may compensate an optical resonance distance according to the wavelength of light emitted from the emission layer EML and increase light emission efficiency. Any of the materials included in the hole transport region HTR may be used as materials included in the hole buffer layer. The electron blocking layer is a layer preventing or reducing electron injection from the electron transport region ETR into the hole transport region HTR.

The emission layer EML may be disposed (e.g., positioned) on the hole transport region HTR. The emission layer EML may emit fluorescent and/or phosphorescent light, and the thickness of the emission layer EML may be, for example, from about 100 Å to about 600 Å.

The emission layer EML may have a single layer formed using a single material, a single layer formed using a plurality of different materials, or a multilayer structure having a plurality of layers formed using a plurality of different materials.

The material of the emission layer EML may be any suitable emission material, without specific limitation, and may be selected from fluoranthene derivatives, pyrene derivatives, arylacetylene derivatives, fluorene derivatives, perylene derivatives, chrysene derivatives, anthracene derivatives, benzoanthracene derivatives, triphenylene derivatives, and the like, and preferably, from pyrene derivatives, perylene derivatives, and anthracene derivatives. For example, as the host material of the emission layer EML, anthracene derivatives represented by Formula 4 may be used:

Formula 4

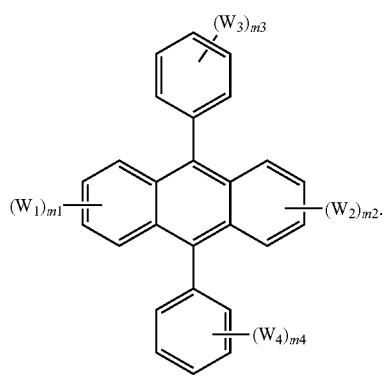

In Formula 4, $W_1$ to $W_4$ may each independently be selected from hydrogen, deuterium, a halogen atom, a substituted or unsubstituted silyl group, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring; m1 and m2 may each independently be an integer of 0 to 4; and m3 and m4 may each independently be an integer of 0 to 5. In Formula 4, $W_3$ and $W_4$ may each independently be combined with an adjacent group to form a saturated or unsaturated ring.

In case when m1 is 2 or more, a plurality of $W_1$ may be the same or different from each other. In case when m2 is 2 or more, a plurality of $W_2$ may be the same or different from each other. In case when m3 is 2 or more, a plurality of $W_3$ may be the same or different from each other. In case when m4 is 2 or more, a plurality of $W_4$ may be the same or different from each other.

The compound represented by Formula 4 may include any of the Compounds a-1 to a-12 represented by the following formulae. However, examples of the compound represented by Formula 4 are not limited thereto.

a-1

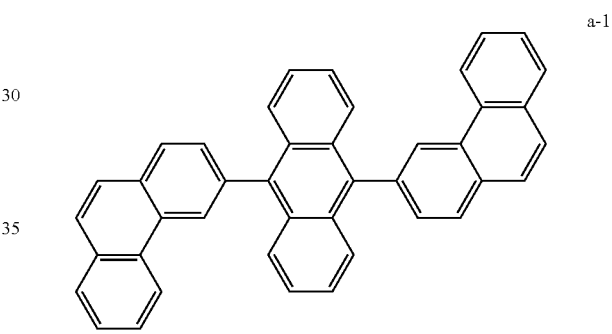

a-2

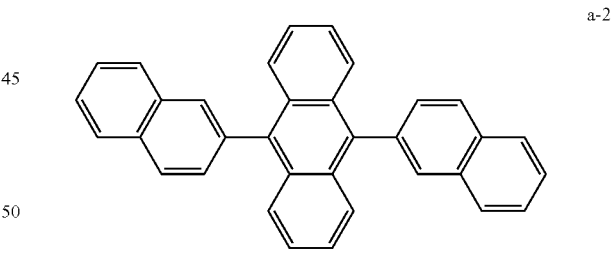

a-3

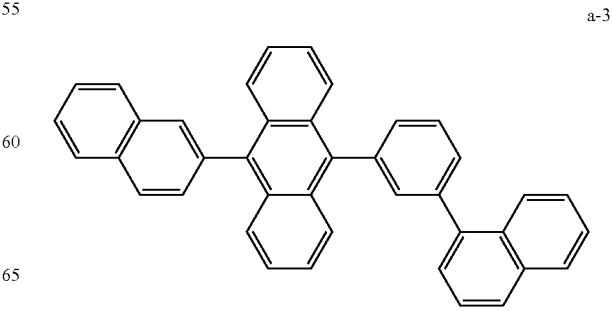

-continued a-4
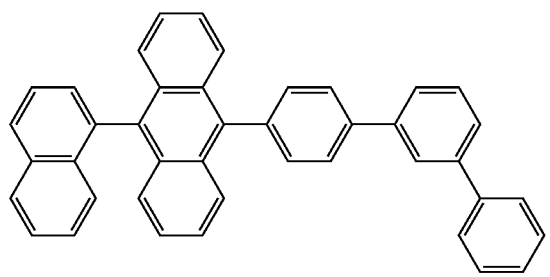

a-5
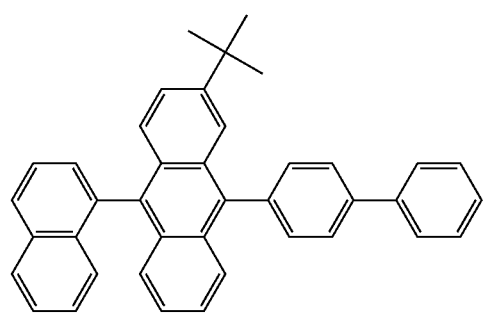

a-6
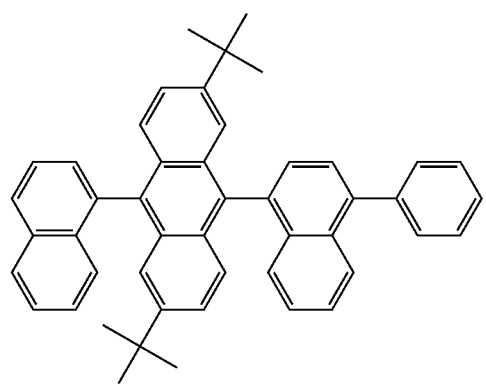

a-7
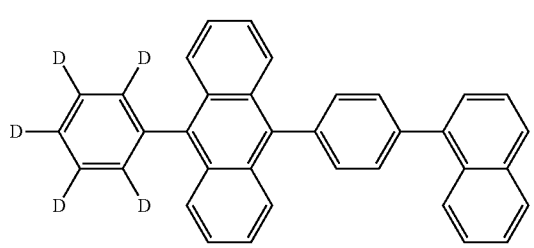

a-8
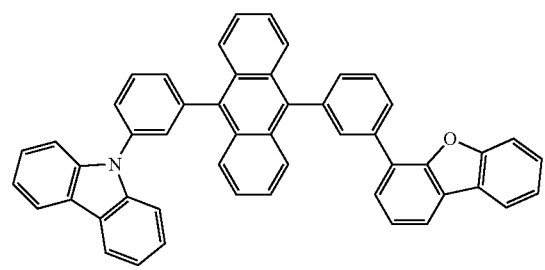

-continued a-9
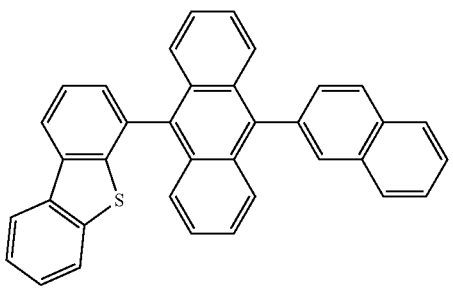

a-10
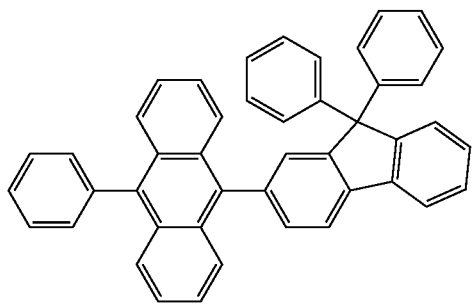

a-11
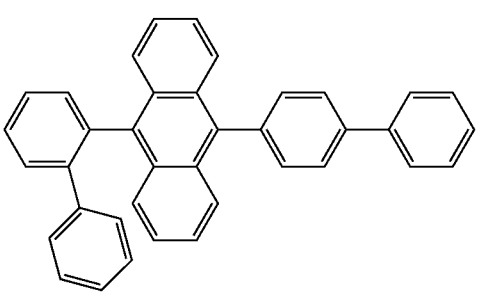

a-12
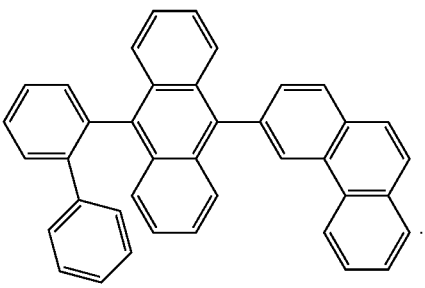

The emission layer EML may include a fluorescent material including any one selected from spiro-DPVBi, 2,2',7,7'-tetrakis(biphenyl-4-yl)-9,9'-spirobifluorene(spiro-sexiphenyl) (spiro-6P), distyryl-benzene (DSB), distyryl-arylene (DSA), polyfluorene (PFO)-based polymer and poly(p-phenylene vinylene) (PPV)-based polymer, for example.

The emission layer EML may further include a dopant, and the material of the dopant may be any suitable material used in the art. The dopant may include, for example, styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (e.g., 2,5,8,11-tetra-t-butylperylene (TBPe)), pyrene and the derivatives thereof (e.g., 1,1-dipyrene, 1,4-dipyrenylbenzene, 1,4-bis(N,N-diphenylamino)pyrene), 2,5,8,11-tetra-t-butylperylene (TBP), 1,3,5-tris(N-phenylbenzimidazol-2-yl)benzene (TPBi), bis[2(4,6-difluorophenyOpyridinato-C²,N](picolinato) (Flrpic)), etc.

The emission layer EML may include, for example, tris(8-hydroxyquinolino)aluminum (Alq$_3$), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 1,3-Bis(N-carbazolyl)benzene (mCP), 2,8-bis(diphenylphosphoryl)dibenzofuran (PPF), etc.

The electron transport region ETR may be provided on the emission layer EML. The electron transport region ETR may include at least one of a hole blocking layer, an electron transport layer ETL and an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In some embodiments, the electron transport region ETR may have a single layer structure having a plurality of different materials, or a laminated structure of electron transport layer ETL/electron injection layer EIL or hole blocking layer/electron transport layer ETL/electron injection layer EIL, laminated (stacked) in this order from the emission layer EML, without limitation. The thickness of the electron transport region ETR may be, for example, from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and/or a laser induced thermal imaging (LITI) method.

In case when the electron transport region ETR includes the electron transport layer ETL, the electron transport region ETR may include tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory (or suitable) electron transport properties may be obtained without substantial increase of a driving voltage.

When the electron transport region ETR includes the electron injection layer EIL, the electron transport region ETR may use LiF, lithium quinolate (LiQ), Li$_2$O, BaO, NaCl, CsF, a metal in lanthanoids such as Yb, and/or metal halides such as RbCl and/or Rbl, without limintation. The electron injection layer EIL also may be formed using a mixture material of an electron transport material and an insulating organo-metal salt. The organo-metal salt may be a material having an energy band gap of about 4 eV or more. In an embodiment, the organo-metal salt may include, for example, a metal acetate, a metal benzoate, a metal acetoacetate, a metal acetylacetonate, and/or a metal stearate. The thickness of the electron injection layer EIL may be from about 1 Å to about 100 Å, for example, from about 3 Å to about 90 Å. In case when the thickness of the electron injection layer EIL satisfies the above described range, satisfactory (or suitable) electron injection properties may be obtained without inducing a substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP) and 4,7-diphenyl-1,10-phenanthroline (Bphen), without limitation.

The second electrode EL2 may be disposed on the electron transport region ETR. The second electrode EL2 may be a common electrode or a cathode. The second electrode EL2 may be a transmissive electrode, a transflective electrode or a reflective electrode. In case when the second electrode EL2 is the transmissive electrode, the second electrode EL2 may be formed using transparent metal oxides, for example, ITO, IZO, ZnO, ITZO, etc.

In case when the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). The second electrode EL2 may have a multilayered structure including a reflective layer or a transflective layer formed using any of the above-described materials and a transparent conductive layer formed using ITO, IZO, ZnO, ITZO, etc.

The thickness of the second electrode EL2 may be from about 700 Å to about 10,000 Å, for example, from about 700 Å to about 2,000 Å.

In an embodiment, the second electrode EL2 may be connected (or coupled) with an auxiliary electrode. In case when the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are then recombined in the emission layer EML to generate excitons, and light may be emitted via the transition of excitons from an excited state to a ground state.

The organic electroluminescence device according to an embodiment of the present disclosure includes the heterocyclic compound represented by Formula 1 in the hole transport region, thereby securing a high efficiency and/or low driving voltage.

Hereinafter, the present disclosure will be explained in more detail with reference to examples and comparative examples. However, the following examples are illustrated only for purpose of assisting in the understanding of the present disclosure, and the scope of the present disclosure is not limited thereto.

Synthesis Examples

The heterocyclic compounds according to an embodiment of the present disclosure were synthesized as follows. However, the synthetic method of the heterocyclic compounds according to an embodiment of the present disclosure is not limited thereto.

1. Synthesis of Compound 1

Compound 1, as the heterocyclic compounds according to an embodiment of the present disclosure, may be synthesized, for example, by the following reaction:

(Synthesis of Compound A)

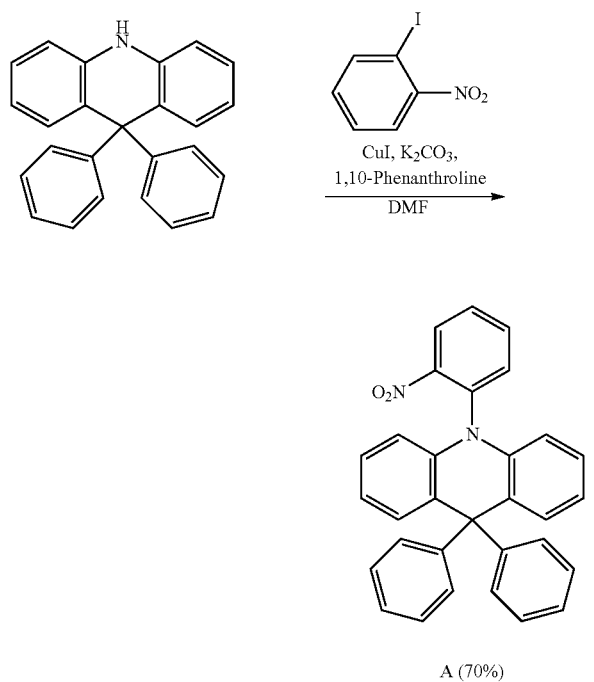

A (70%)

Under an argon (Ar) atmosphere, 2.20 g of 9,10-dihydro-9,9-diphenylacridine, 1.97 g of 1-iodo-2-nitrobenzene, 0.93 g of $K_2CO_3$, 0.25 g of CuI and 1.03 g of 1,10-phenanthroline dissolved in DMF were injected into a 200 mL three neck flask, and the mixture was stirred and heated at about 155° C. for about 6 hours. After air cooling the resulting mixture, ethyl acetate and water was added thereto. An organic layer was separated and taken therefrom, and solvents were evaporated therefrom. The crude product thus obtained was purified by silica gel column chromatography (solvent: hexane/AcOEt) to obtain 2.10 g (yield 70%) of Compound A as a yellow solid.

The molecular weight of Compound A measured by Fast Atom Bombardment Mass Spectrometry (FAB-MS) was 454.

(Synthesis of Compound B)

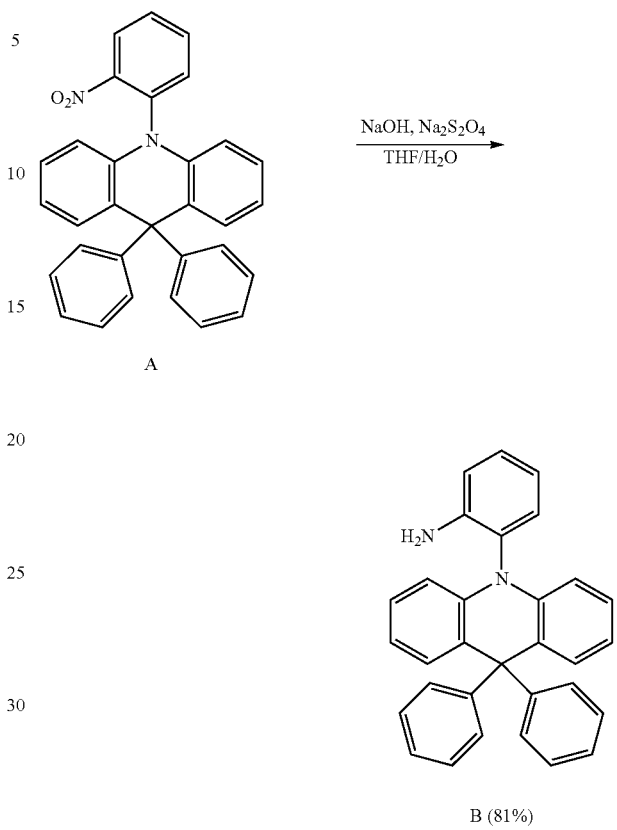

B (81%)

In an atmospheric condition, 2.27 g of Compound A, 0.47 g of NaOH and 0.80 g of $Na_2S_2O_4$ were added to 45 mL of 50% THF aqueous solution in an 100 mL three neck flask, and the mixture was stirred and heated to reflux for about 3 hours. After air cooling the resulting mixture, AcOEt and water were added thereto. An organic layer was separated and taken therefrom, and solvents were evaporated therefrom. The crude product thus obtained was purified by silica gel column chromatography (solvent: toluene) to obtain 1.72 g (yield 81%) of Compound B as a yellow solid.

The molecular weight of Compound B measured by FAB-MS was 424.

(Synthesis of Compound C)

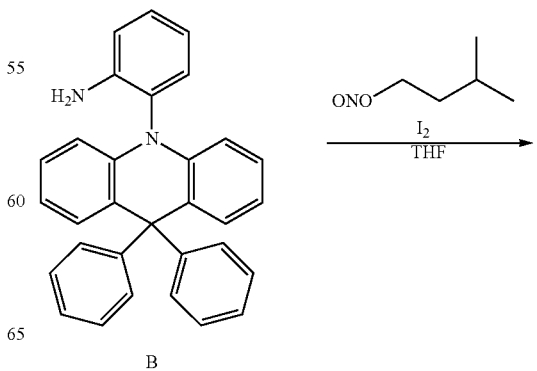

B

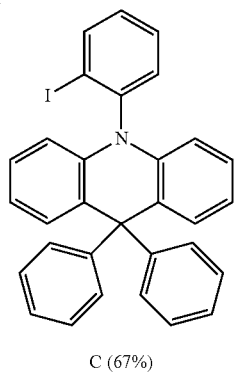

C (67%)

Under an argon (Ar) atmosphere, 2.12 g of Compound B, 1.00 g of isopentyl nitrite and 2.13 g of iodine were added to 20 mL of toluene in a 50 mL three neck flask, and the mixture was stirred at room temperature. After air cooling the resulting mixture, water was added thereto. An organic layer was separated and taken therefrom, and solvents were evaporated therefrom. The crude product thus obtained was purified by silica gel column chromatography (solvent: hexane/toluene) to obtain 1.79 g (yield 67%) of Compound C as a white solid.

The molecular weight of Compound C measured by FAB-MS was 535.

(Synthesis of Compound D)

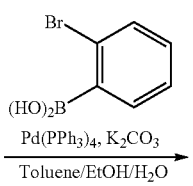

C

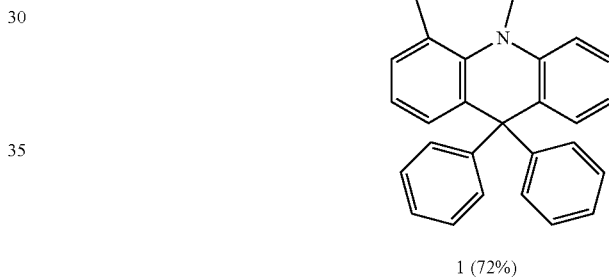

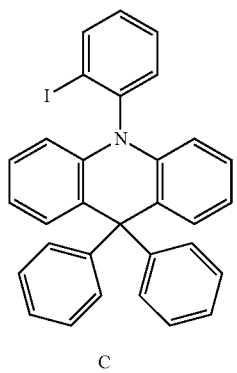

D (75%)

Under an argon (Ar) atmosphere, 5.35 g of Compound C, 2.10 g of 2-bromophenylboronic acid, 0.33 g of Pd(PPh$_3$)$_4$ and 2.30 g of K$_2$CO$_3$ were added to a mixture of 100 mL toluene, 10 mL EtOH and 20 mL water in an 100 mL three neck flask, and the mixture was stirred and heated to reflux for about 3 hours. After air cooling the resulting mixture, water was added thereto. An organic layer was separated and taken therefrom, and solvents were evaporated therefrom. The crude product thus obtained was purified by silica gel column chromatography (solvent: hexane/toluene) to obtain 4.18 g (yield 75%) of Compound D as a white solid.

The molecular weight of Compound D measured by FAB-MS was 565.

(Synthesis of Compound 1)

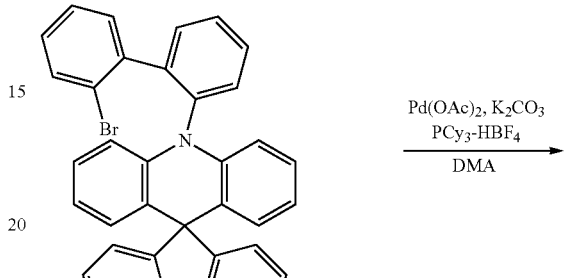

D

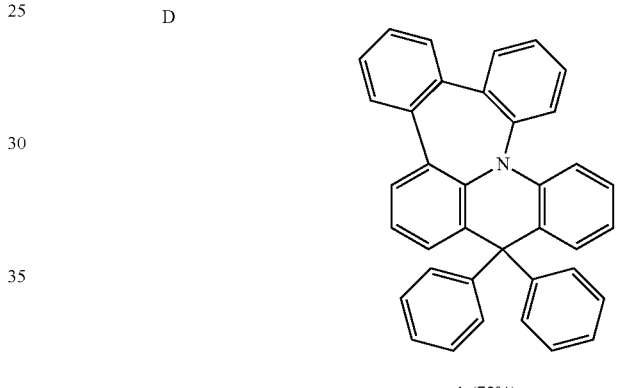

1 (72%)

Under an argon (Ar) atmosphere, 2.83 g of Compound D, 0.24 g of Pd(OAc)$_2$, 1.41 g of K$_2$CO$_3$ and 0.081 g of PCy$_3$-HBF$_4$ were added to 20 mL of DMA in a 50 mL three neck flask, and the mixture was stirred and heated to reflux for about 6 hours. After air cooling the resulting mixture, water was added thereto. An organic layer was separated and taken therefrom, and solvents were evaporated therefrom. The crude product thus obtained was purified by silica gel column chromatography (solvent: a mixture of toluene and hexane) to obtain 1.74 g (yield 72%) of Compound 1 as a white solid.

The molecular weight of Compound 1 measured by FAB-MS was 483. The chemical shift (δ) values of Compound 1 measured by $^1$H-NMR (CDCl$_3$) were 8.55 (dd, 2H, J=7.10 Hz), 8.41 (d, 1H, J=7.82 Hz), 8.25 (dd, 4H, J=7.20 Hz), 8.10 (d, 2H, J=7.80 Hz), 8.02-7.89 (m, 3H), 7.69-7.62 (m, 7H), 7.48-7.43 (m, 3H), 7.41-7.25 (m, 3H).

2. Synthesis of Compound 2

Compound 2 was synthesized by conducting the same (or substantially the same) synthetic method as the one utilized for Compound 1, except for using 9,10-dihydro-2,7,9,9-tetraphenylacridine instead of 9,10-dihydro-9,9-diphenylacridine used in the synthetic method of Compound 1. The molecular weight of Compound 2 measured by FAB-MS was 636. The chemical shift (δ) values of Compound 1 measured by $^1$H-NMR (CDCl$_3$) were 8.55 (dd, 2H, J=7.00

Hz), 8.41 (d, 1H, J=7.62 Hz), 8.26 (dd, 4H, J=7.20 Hz), 8.11 (d, 2H, J=7.80 Hz), 8.02-7.89 (m, 3H), 7.67-7.62 (m, 7H), 7.52-7.43 (m, 8H), 7.41-7.30 (m, 8H).

3. Synthesis of Compound 15

Compound 15 was synthesized by conducting the same (or substantially the same) synthetic method as the one utilized for Compound 1, except for using 3,7-bis(4-dibenzofuranyl)-10H-phenoxazine instead of 9,10-dihydro-9,9-diphenylacridine used in the synthetic method of Compound 1. The molecular weight of Compound 15 measured by FAB-MS was 666. The chemical shift (δ) values of Compound 1 measured by $^1$H-NMR (CDCl$_3$) were 8.45 (dd, 2H, J=7.10 Hz), 8.33 (d, 1H, J=7.82 Hz), 8.23 (dd, 4H, J=7.20 Hz), 8.12 (d, 2H, J=7.70 Hz), 8.04-7.91 (m, 5H), 7.69-7.62 (m, 7H), 7.52-7.45 (m, 8H), 7.41-7.30 (m, 8H).

4. Synthesis of Compound 26

Compound 26 was synthesized by conducting the same (or substantially the same) synthetic method as the one utilized for Compound 1, except for using 5,10-dihydro-10,10-diphenylphenazasiline instead of 9,10-dihydro-9,9-diphenylacridine used in the synthetic method of Compound 1. The molecular weight of Compound 26 measured by FAB-MS was 652. The chemical shift (δ) values of Compound 1 measured by $^1$H-NMR (CDCl$_3$) were 8.44 (dd, 2H, J=7.30 Hz), 8.40 (d, 1H, J=7.82 Hz), 8.36 (dd, 4H, J=7.20 Hz), 8.11 (d, 2H, J=7.80 Hz), 8.02-7.89 (m, 3H), 7.77-7.62 (m, 7H), 7.52-7.43 (m, 8H), 7.41-7.35 (m, 8H).

In Synthesis Examples 1 to 4, the molecular weight of compounds was measured by FAB-MS using JMS-700V (JEOL Ltd.). NMR of compounds was measured by $^1$H-NMR using AVANCE300M (Bruker Biospin K.K.).

Device Manufacturing Examples

Organic electroluminescence devices of Examples 1 to 4 were manufactured by using the above Compounds 1, 2, 15 and 26, respectively, as hole transport layer materials.

Example Compounds

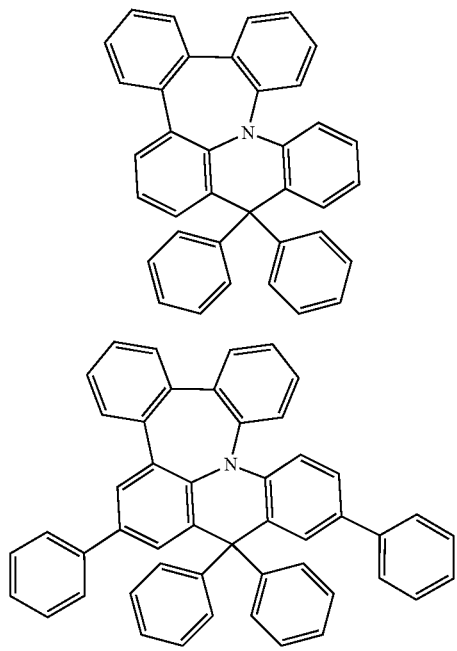

-continued

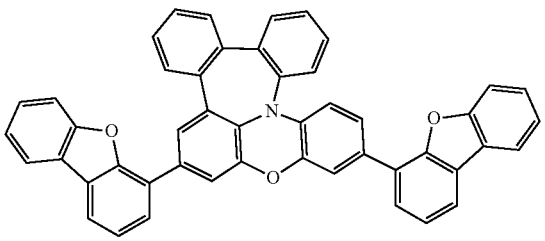

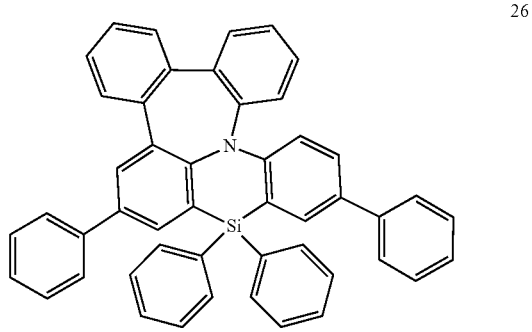

Organic electroluminescent devices of Comparative Examples 1 to 5 were manufactured by using the following Comparative Compounds A-1 to A-5, respectively, as hole transport layer materials.

Comparative Compounds

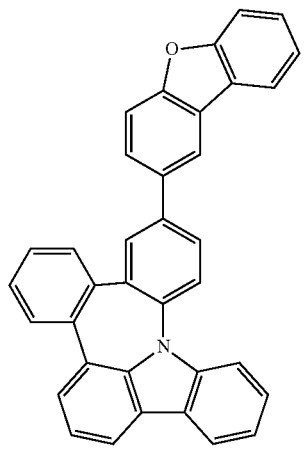

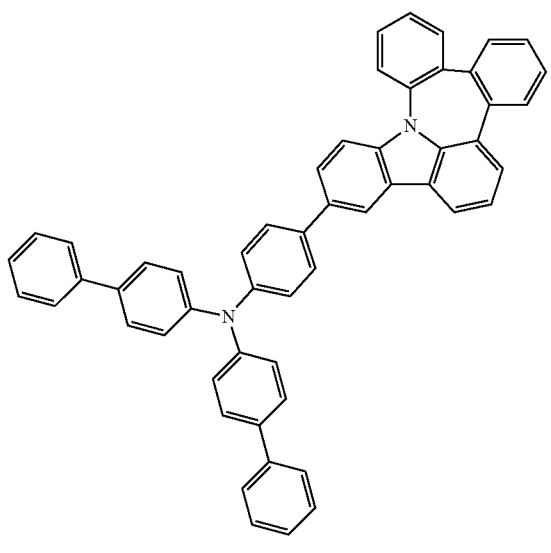

A-2

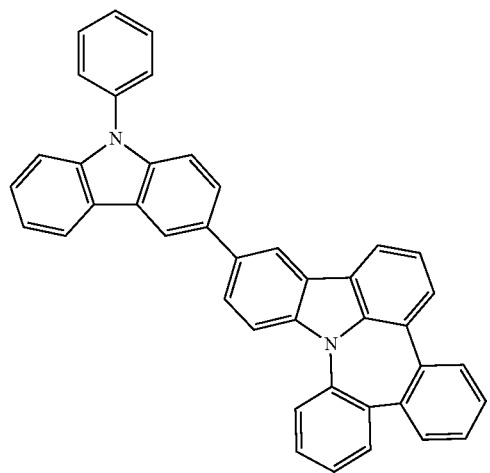

A-3

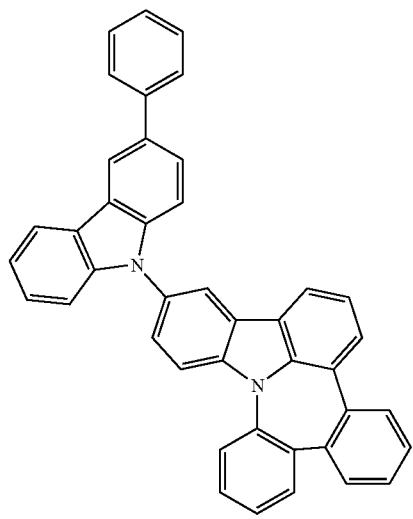

A-4

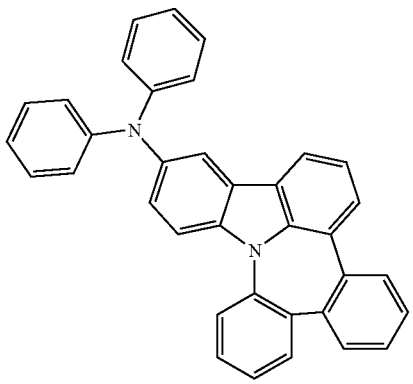

A-5

The organic electroluminescence devices according to Examples 1 to 4 and Comparative Examples 1 to 5 were each manufactured by forming a first electrode using ITO to a thickness of about 150 nm, a hole injection layer using TNATA to a thickness of about 60 nm, a hole transport layer using the respective example compound or comparative compound to a thickness of about 30 nm, an emission layer using 9,10-di(naphthalen-2-yl)anthracene (ADN) doped with 3% 2,5,8,11-tetra-t-butylpherylene (TBP) to a thickness of about 25 nm, an electron transport layer using $Alq_3$ to a thickness of about 25 nm, an electron injection layer using LiF to a thickness of about 1 nm, and a second electrode using Al to a thickness of about 100 nm. Each layer was formed by a vacuum deposition method.

The current density, driving voltage and emission efficiency of the manufactured organic electroluminescence devices were evaluated. Evaluation results are shown in Table 1 below.

TABLE 1

| Device manufacturing example | Hole transport layer material | Current density (mA/cm$^2$) | Driving voltage (V) | Emission efficiency (cd/A) |
|---|---|---|---|---|
| Example 1 | Example Compound 1 | 10 | 5.5 | 6.5 |
| Example 2 | Example Compound 2 | 10 | 5.6 | 6.7 |
| Example 3 | Example Compound 15 | 10 | 5.6 | 6.6 |
| Example 4 | Example Compound 26 | 10 | 5.4 | 6.5 |
| Comparative Example 1 | Comparative Compound A-1 | 10 | 6.2 | 5.2 |
| Comparative Example 2 | Comparative Compound A-2 | 10 | 6.5 | 5.1 |
| Comparative Example 3 | Comparative Compound A-3 | 10 | 6.2 | 5.2 |
| Comparative Example 4 | Comparative Compound A-4 | 10 | 6.4 | 5.3 |
| Comparative Example 5 | Comparative Compound A-5 | 10 | 6.4 | 5.2 |

Referring to the results shown in Table 1, it may be found that the heterocyclic compound according to an embodiment of the present disclosure may improve the emission efficiency of the device. In addition, it may decrease driving voltage of the device.

Specifically, it may be found that the organic electroluminescence devices of Examples 1 to 4 have a low driving voltage and high efficiency as compared with those of Comparative Examples 1 to 5.

The heterocyclic compound according to an embodiment of the present disclosure has dibenzoazepinodihydroacridine moiety, thereby attaining a low driving voltage and high efficiency. Dihydroacridine was originally known as a hole transport material with long life. Without being bound by any particular theory, it is believed that by crosslinking dihydroacridine radical and phenyl radical with benzene ring, nitrogen electrons spread into phenyl radical which is substituted at dihydroacridine and has an inherently low conjugate effect, thereby enhancing hole transport property and attaining low driving voltage and high efficiency. The organic electroluminescence devices of Comparative Examples 1 to 5 having a dibenz[4,5:6,7]azepino[3,2,1-jk] carbazole moiety, and not a dihydroacridine moiety, have relatively low (e.g., inferior) hole transport property as compared with those of Examples 1 to 4, and consequently low efficiency.

The heterocyclic compound according to an embodiment of the present disclosure may have excellent emission efficiency.

Thus, the organic electroluminescence device including the heterocyclic compound according to an embodiment of the present disclosure may attain high emission efficiency.

The organic electroluminescence device including the heterocyclic compound according to an embodiment of the present disclosure may attain a low driving voltage effect.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although example embodiments of the present invention have been described herein, it will be understood that the present invention should not be limited to these example embodiments, but various changes and modifications can be made by one ordinary skilled in the art within the spirit and scope of the present invention as hereinafter claimed in the appended claims and equivalents thereof.

What is claimed is:

1. A heterocyclic compound represented by the following Formula 1:

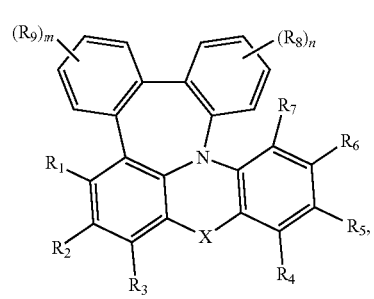

Formula 1 wherein in Formula 1,

X is O, S, $NR_{10}$, $CR_{11}R_{12}$ or $SiR_{13}R_{14}$, $R_1$ to $R_4$, $R_6$, $R_7$, and $R_{10}$ to $R_{14}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring, $R_5$ is a substituted or unsubstituted aryl group having 6 to 30 carbon atoms for forming a ring, or a substituted or unsubstituted heterocyclic group having 2 to 30 carbon atoms for forming a ring, $R_8$ and $R_9$ are each hydrogen, and m and n are each independently an integer of 0 to 4.

2. The heterocyclic compound of claim 1, wherein Formula 1 is represented by the following Formula 2:

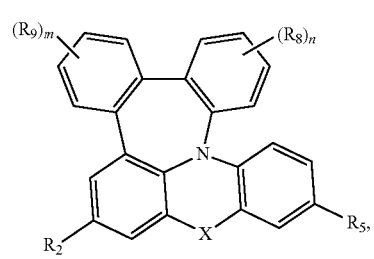

Formula 2 wherein in Formula 2, definitions for X, $R_2$, $R_5$, $R_8$, $R_9$, n and m are the same as those in Formula 1.

3. The heterocyclic compound of claim 2, wherein at least one of $R_2$ or $R_5$ is a substituted or unsubstituted phenyl group, a substituted or unsubstituted naphthyl group, a substituted or unsubstituted carbazole group, or a substituted or unsubstituted dibenzofuranyl group.

4. The heterocyclic compound of claim 1, wherein $R_5$ is represented by the following Formula 3:

Formula 3

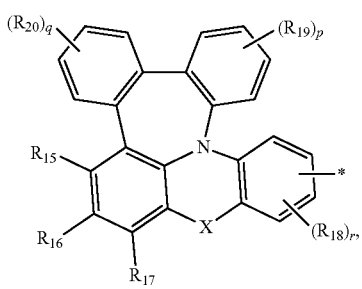

Compound Group1

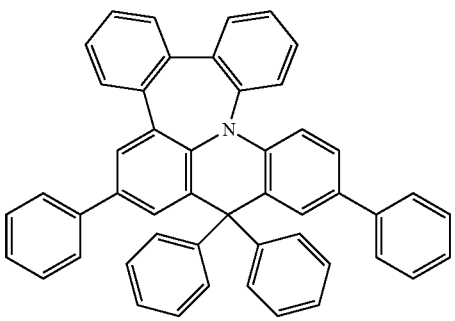

2

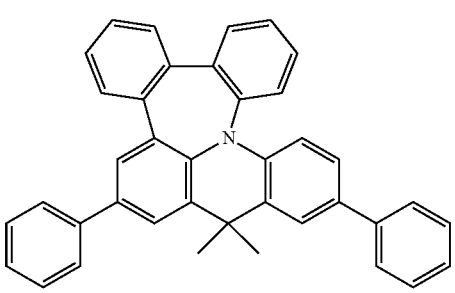

3

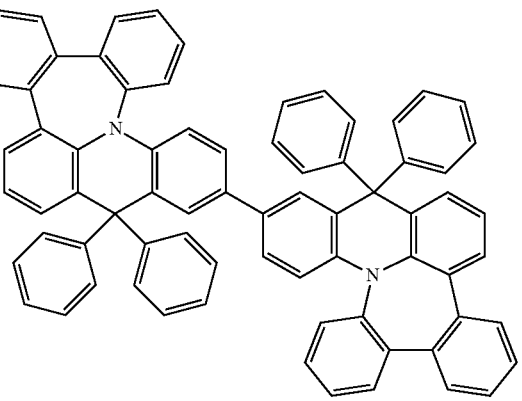

5

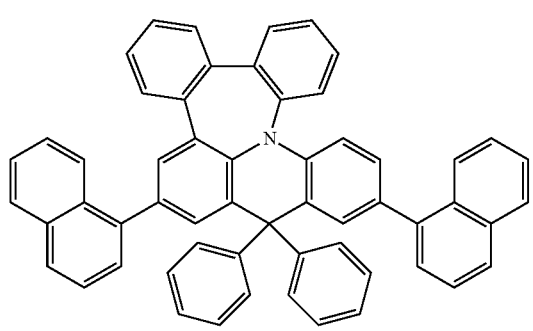

6 wherein in Formula 3,

Y is O, S, $NR_{21}$, $CR_{22}R_{23}$ or $SiR_{24}R_{25}$, $R_{15}$ to $R_{25}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring, $R_{22}$ and $R_{24}$ each independently optionally form a ring by combining with $R_{23}$ and $R_{25}$, respectively, r is an integer of 0 to 3, and p and q are each independently an integer of 0 to 4.

5. The heterocyclic compound of claim 4, wherein X and Y are the same as each other.

6. The heterocyclic compound of claim 1, wherein X is $CR_{11}R_{12}$, and $R_{11}$ and $R_{12}$ are each independently a substituted or unsubstituted alkyl group having 1 to 20 carbon atoms, or a substituted or unsubstituted aryl group having 6 to 30 carbon atoms for forming a ring, wherein $R_{11}$ and $R_{12}$ optionally form a ring by combining with each other.

7. The heterocyclic compound of claim 1, wherein X is O.

8. The heterocyclic compound of claim 1, wherein X is S.

9. The heterocyclic compound of claim 1, wherein X is $SiR_{13}R_{14}$, and $R_{13}$ and $R_{14}$ are each independently a substituted or unsubstituted alkyl group having 1 to 20 carbon atoms, or a substituted or unsubstituted aryl group having 6 to 30 carbon atoms for forming a ring, wherein $R_{13}$ and $R_{14}$ optionally form a ring by combining with each other.

10. The heterocyclic compound of claim 1, wherein the heterocyclic compound represented by Formula 1 is any one selected from the group consisting of Compounds 2, 3, 5 to 24, 26, 27, and 29 to 32, collectively denoted as Compound Group 1:

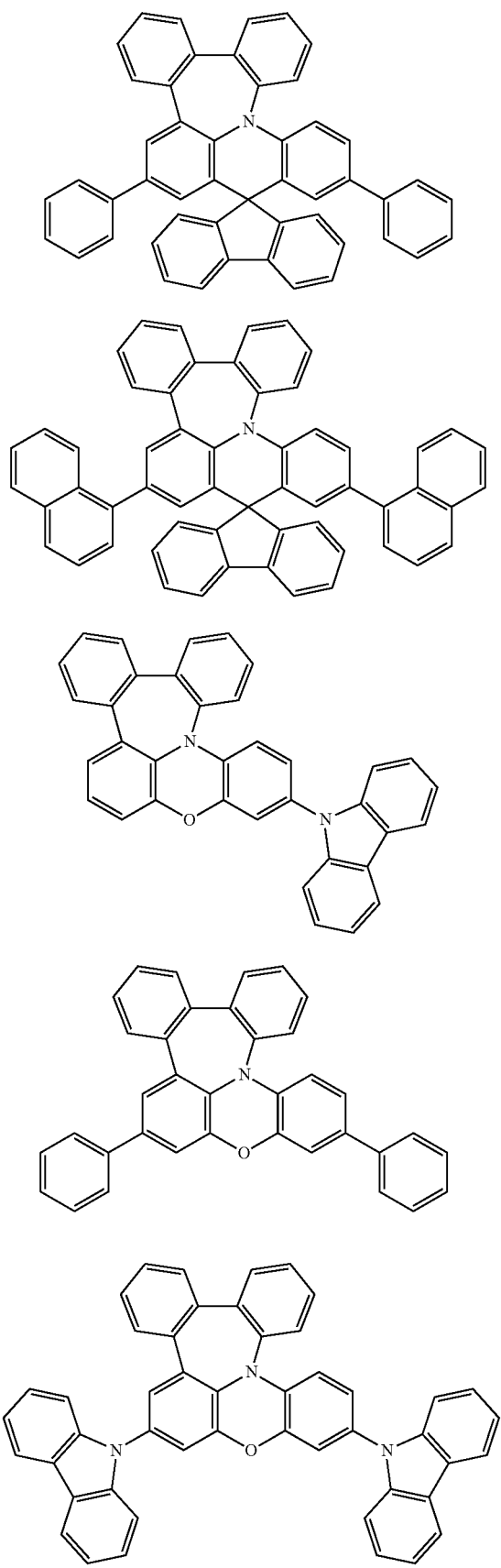
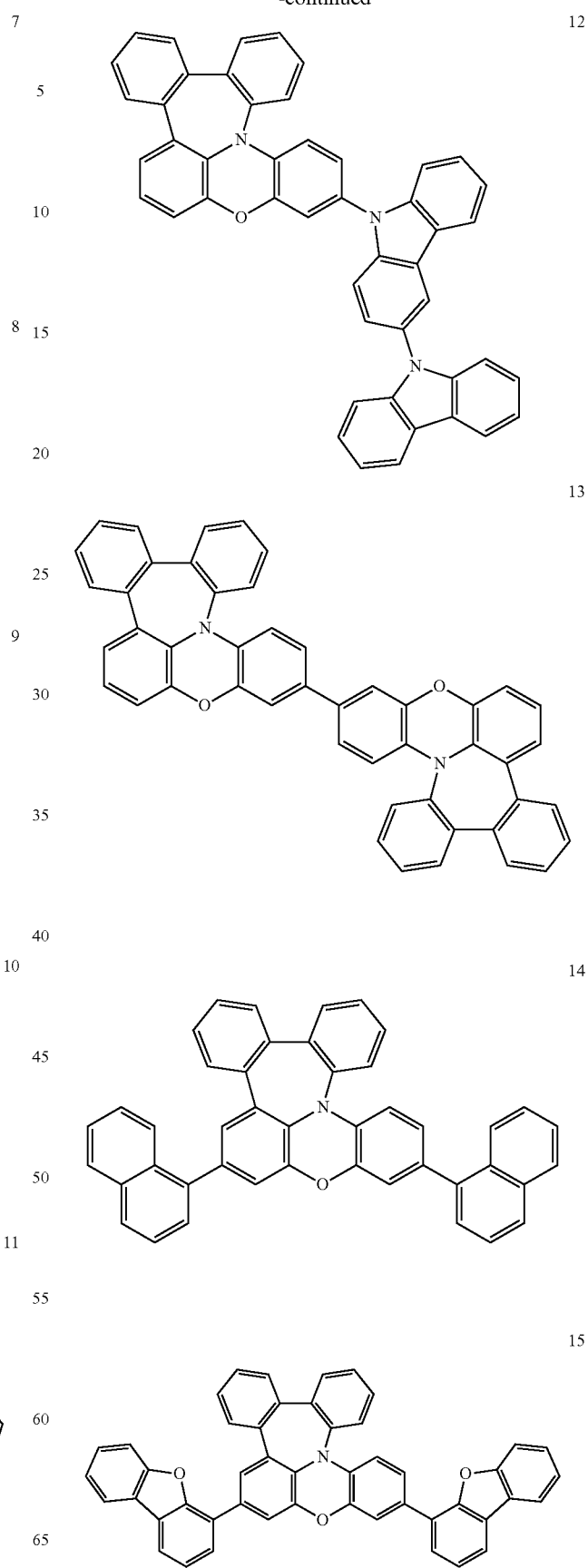

16
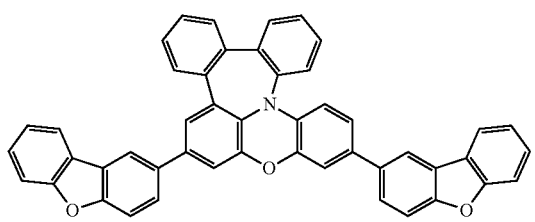
17
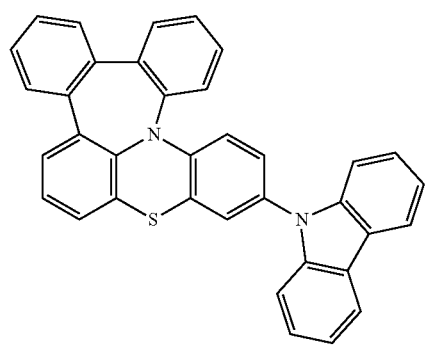
18
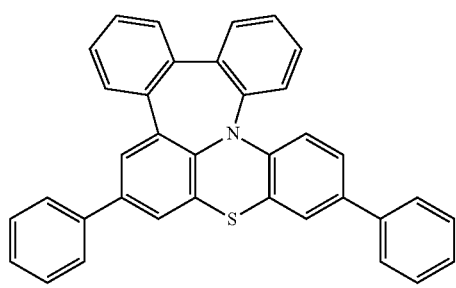
19
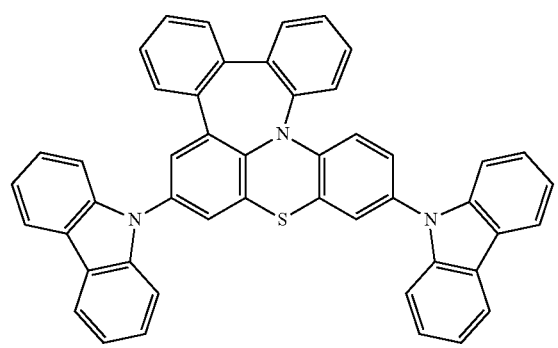
20
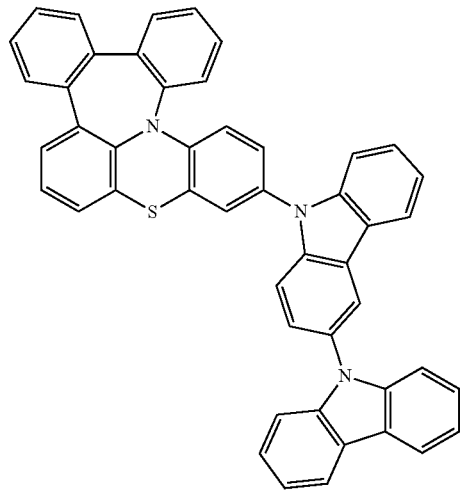
21
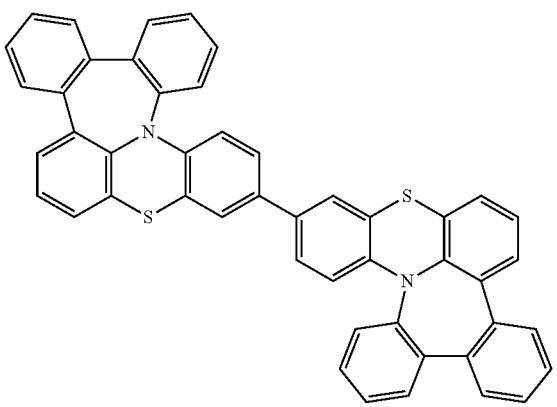
22
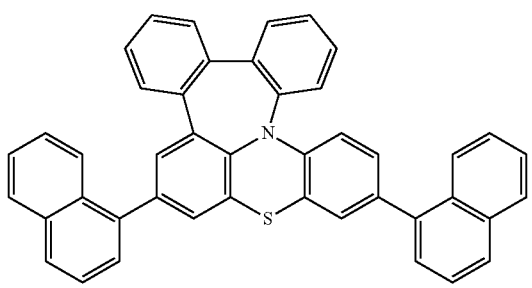
23
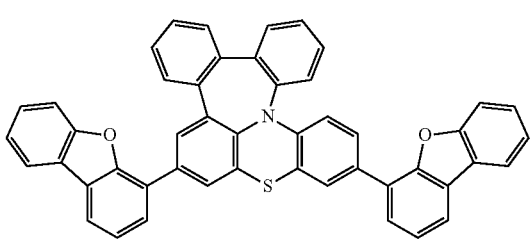

24

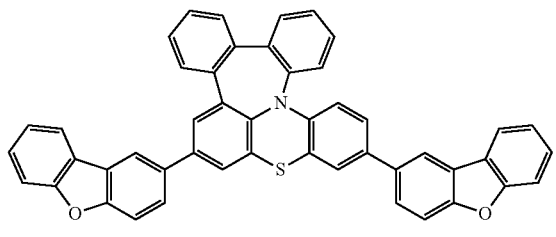

26

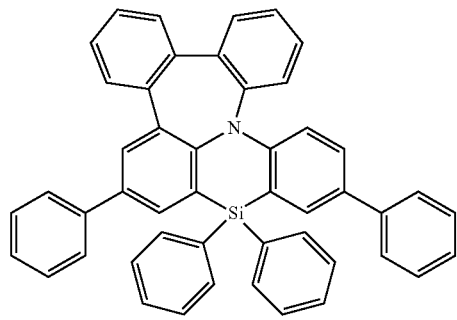

27

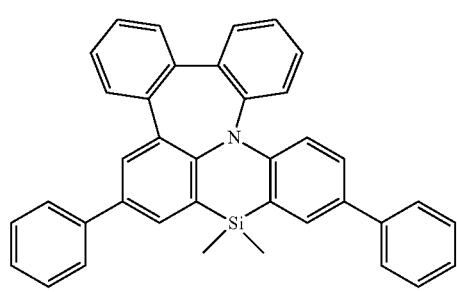

29

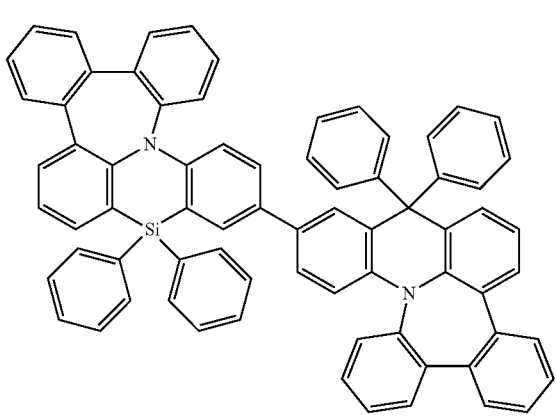

30

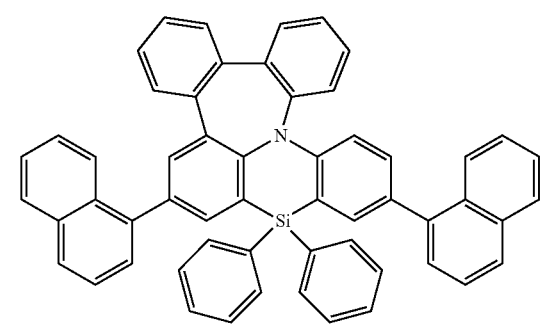

31

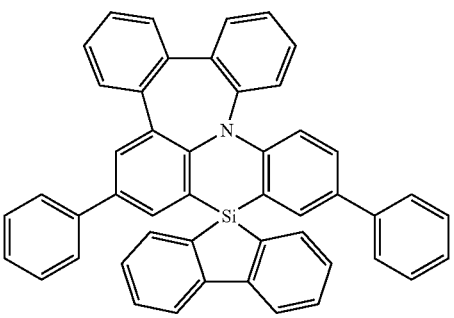

32

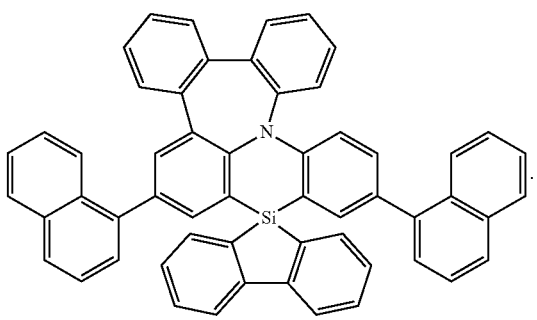

11. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region comprises a heterocyclic compound represented by the following Formula 1:

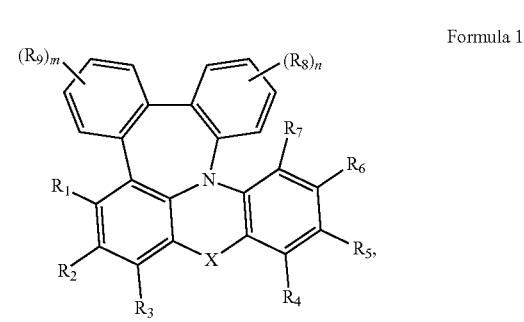

Formula 1 wherein in Formula 1,

X is O, S, $NR_{10}$, $CR_{11}R_{12}$ or $SiR_{13}R_{14}$, $R_1$ to $R_4$, $R_6$, $R_7$, and $R_{10}$ to $R_{14}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring, $R_8$ and $R_9$ are each hydrogen, $R_{11}$ and $R_{13}$ each independently optionally form a ring by combining with $R_{12}$ and $R_{14}$, respectively, and m and n are each independently an integer of 0 to 4.

12. The organic electroluminescence device of claim 11, wherein the hole transport region comprises:
a hole injection layer on the first electrode; and
a hole transport layer on the hole injection layer, and the hole transport layer comprises the heterocyclic compound represented by Formula 1.

13. The organic electroluminescence device of claim 11, wherein Formula 1 is represented by the following Formula 2:

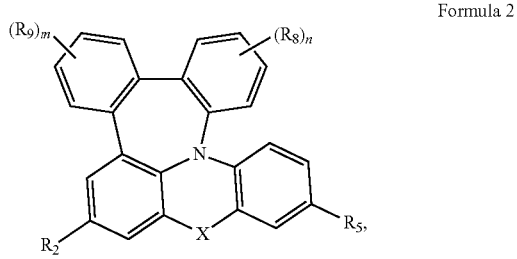

Formula 2 wherein in Formula 2,
definitions for X, $R_2$, $R_5$, $R_8$, $R_9$, n and m are the same as in Formula 1.

14. The organic electroluminescence device of claim 11, wherein at least one of $R_2$ or $R_5$ is a substituted or unsubstituted phenyl group, a substituted or unsubstituted naphthyl group, a substituted or unsubstituted carbazole group, or a substituted or unsubstituted dibenzofuranyl group.

15. The organic electroluminescence device of claim 11, wherein $R_5$ is represented by the following Formula 3:

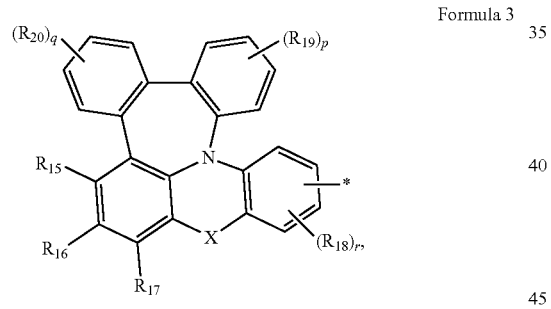

Formula 3 wherein in Formula 3,
Y is O, S, $NR_{21}$, $CR_{22}R_{23}$ or $SiR_{24}R_{25}$,
$R_{15}$ to $R_{25}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heterocyclic group having 2 to 30 carbon atoms for forming a ring,
$R_{22}$ and $R_{24}$ each independently optionally form a ring by combining with $R_{23}$ and $R_{25}$, respectively,
r is an integer of 0 to 3, and
p and q are each independently an integer of 0 to 4.

16. The organic electroluminescence device of claim 11, wherein X is $CR_{11}R_{12}$, and
$R_{11}$ and $R_{12}$ are each independently a substituted or unsubstituted alkyl group having 1 to 20 carbon atoms, or a substituted or unsubstituted aryl group having 6 to 30 carbon atoms for forming a ring, wherein $R_{11}$ and $R_{12}$ optionally form a ring by combining with each other.

17. The organic electroluminescence device of claim 11, wherein X is O.

18. The organic electroluminescence device of claim 11, wherein X is S.

19. The organic electroluminescence device of claim 11, wherein X is $SiR_{13}R_{14}$, and
$R_{13}$ and $R_{14}$ are each independently a substituted or unsubstituted alkyl group having 1 to 20 carbon atoms, or a substituted or unsubstituted aryl group having 6 to 30 carbon atoms for forming a ring, wherein $R_{13}$ and $R_{14}$ optionally form a ring by combining with each other.

20. The organic electroluminescence device of claim 11, wherein the heterocyclic compound represented by Formula 1 is any one selected from the group consisting of Compounds 2, 3, 5 to 24, 26, 27 and 29 to 32, collectively denoted as Compound Group 1:

Compound Group 1

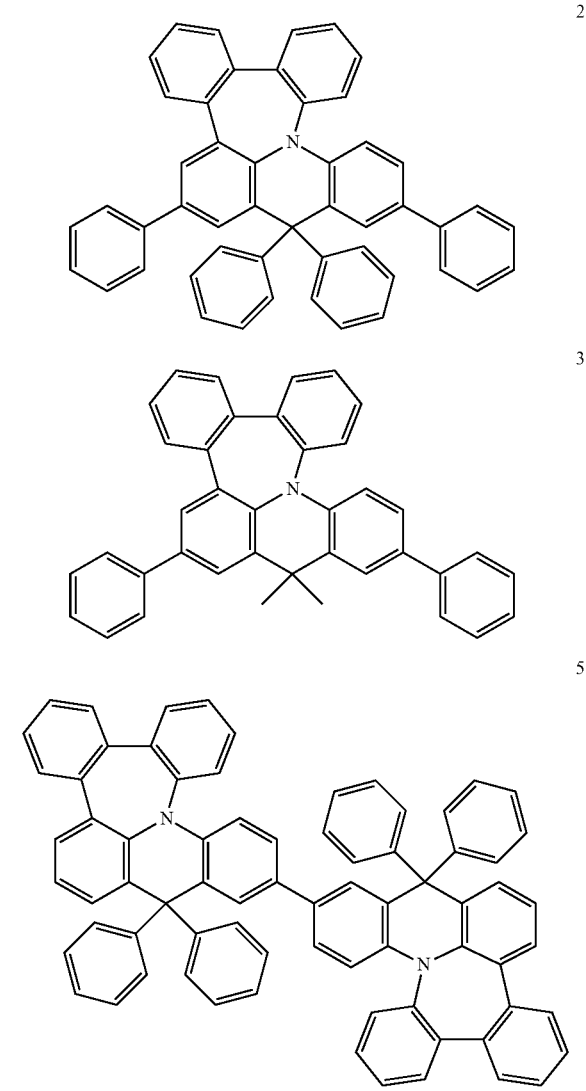

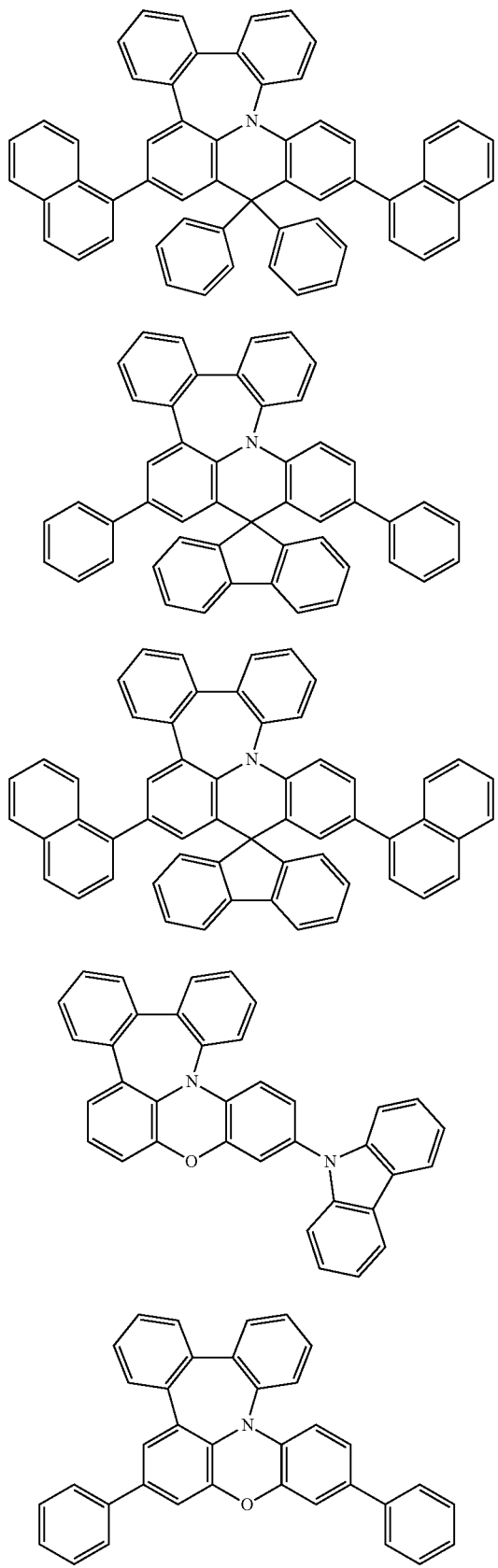
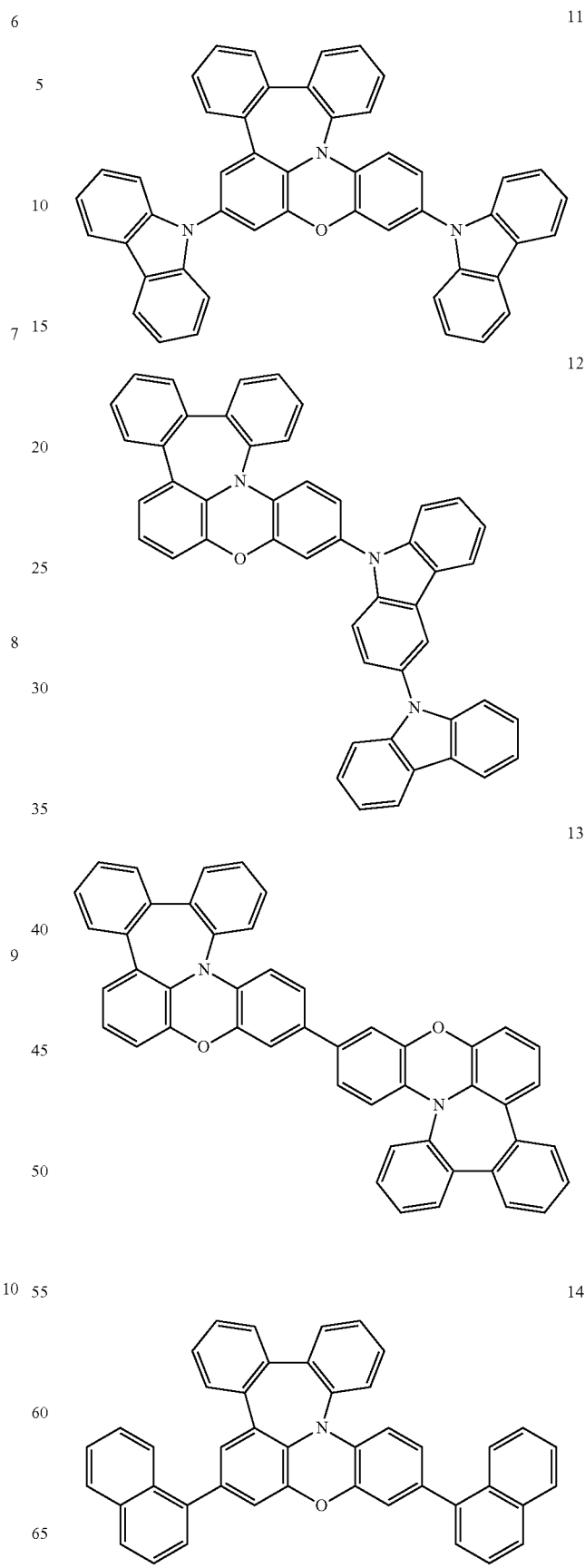

15
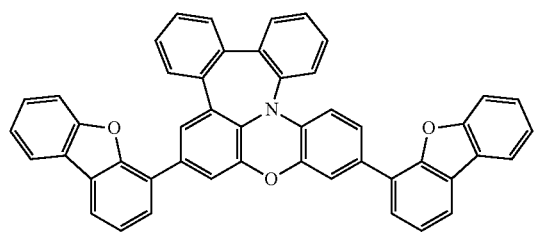
16
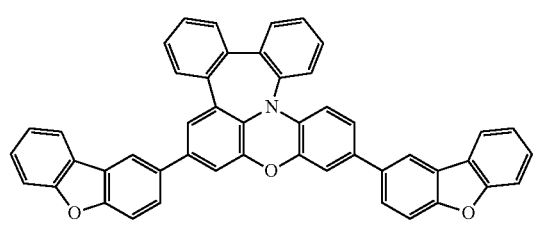
17
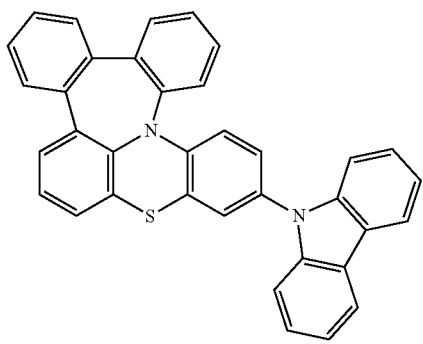
18
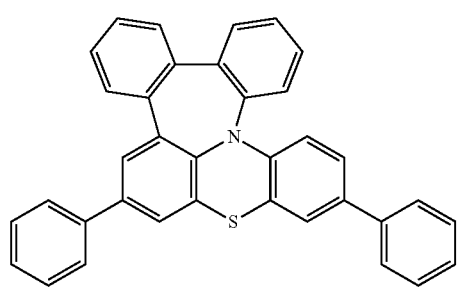
19
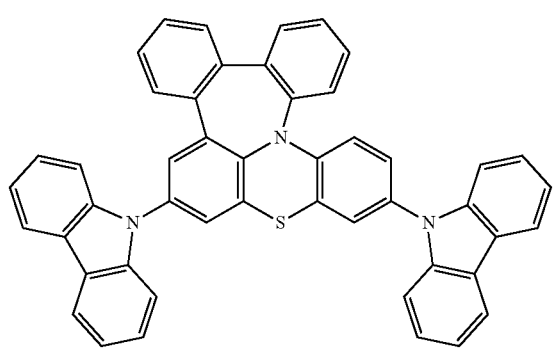
20
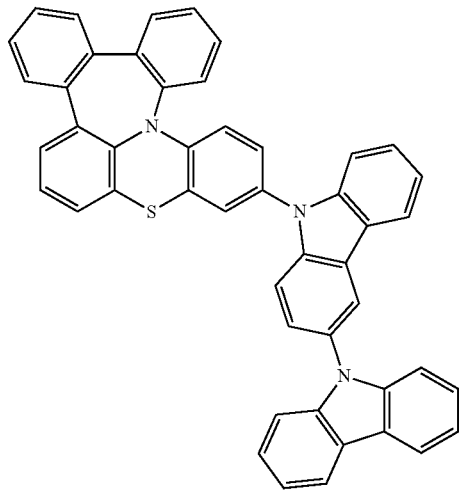
21
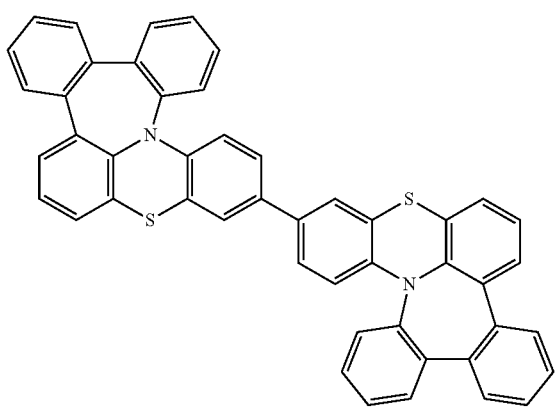
22
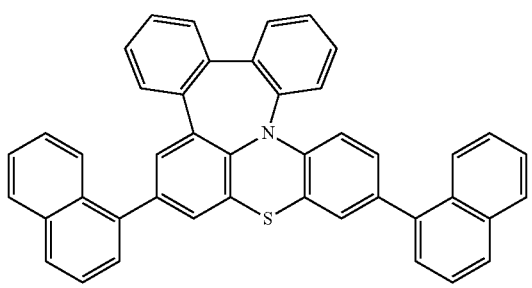
23
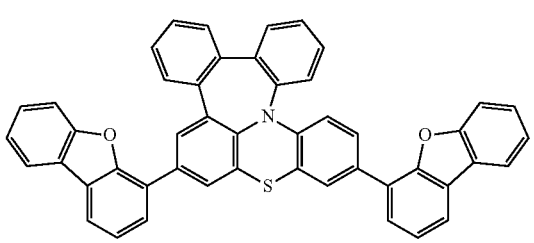

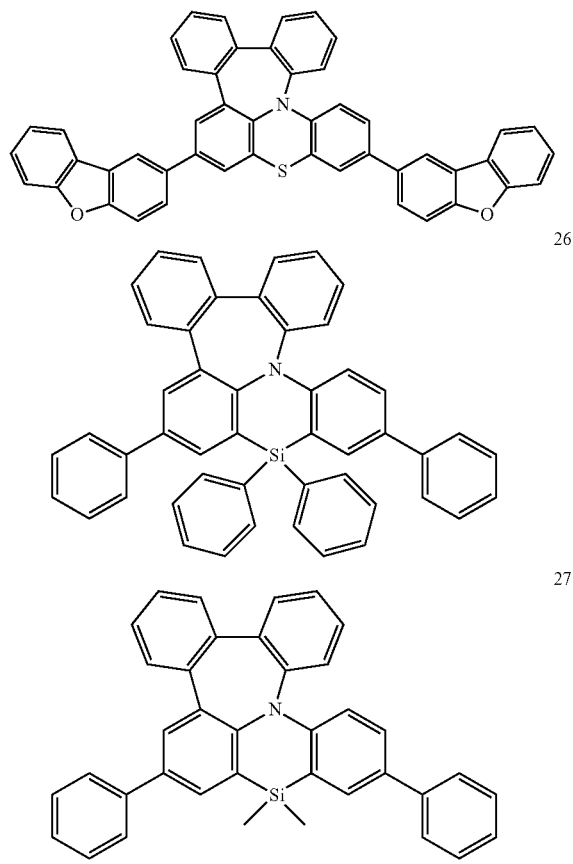
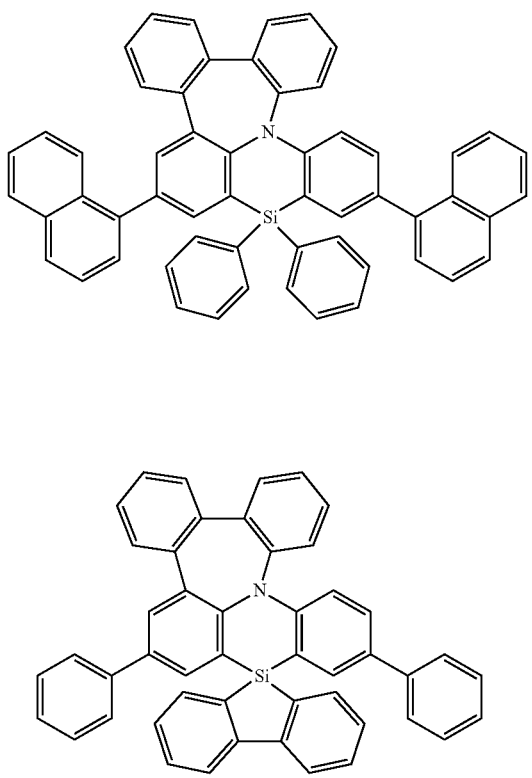
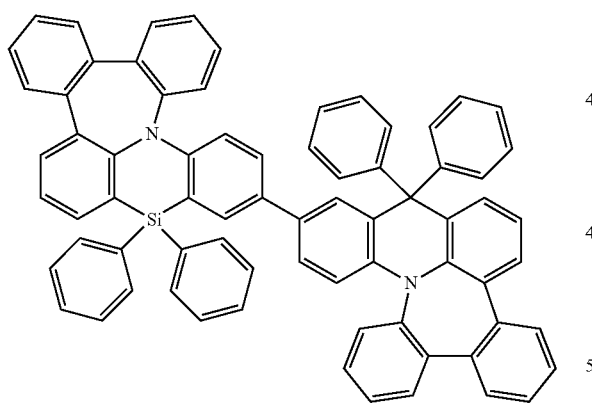
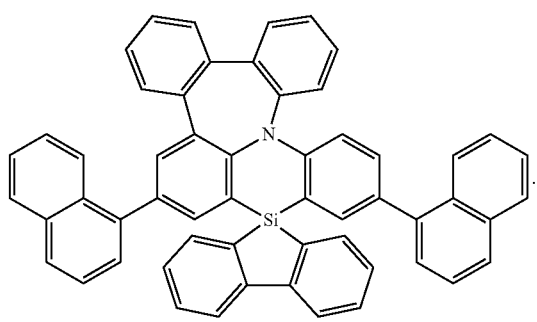
* * * * *

UNITED STATES PATENT AND TRADEMARK OFFICE
CERTIFICATE OF CORRECTION

PATENT NO. : 10,844,059 B2
APPLICATION NO. : 15/805012
DATED : November 24, 2020
INVENTOR(S) : Hiroaki Itoi Page 1 of 1

It is certified that error appears in the above-identified patent and that said Letters Patent is hereby corrected as shown below:

In the Claims

In Column 43, Lines 35-44 (approx.), Claim 15, delete " 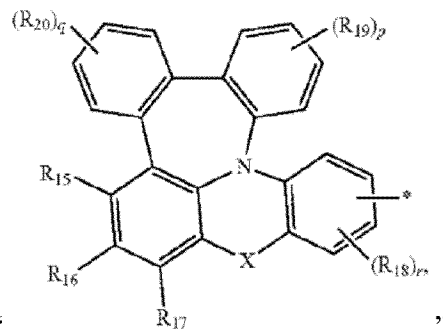 " and insert -- 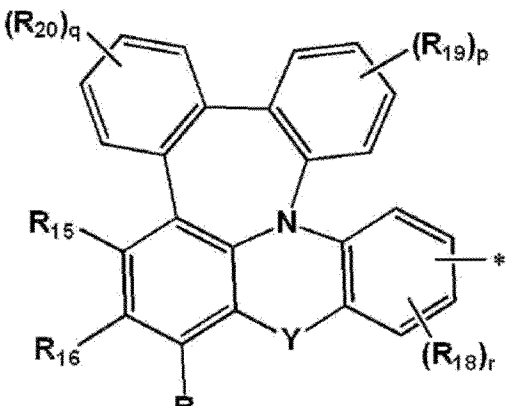 --, therefor.

In Column 44, Line 18, Claim 20, delete "27and" and insert -- 27, and --, therefor.

Signed and Sealed this
Twenty-fourth Day of May, 2022

*Katherine Kelly Vidal*
Katherine Kelly Vidal
*Director of the United States Patent and Trademark Office*